(12) United States Patent
Villard et al.

(10) Patent No.: US 7,747,315 B2
(45) Date of Patent: Jun. 29, 2010

(54) METHODS AND COMPOSITIONS TO REDUCE SCATTERING OF LIGHT DURING THERAPEUTIC AND DIAGNOSTIC IMAGING PROCEDURES

(75) Inventors: Joseph W. Villard, St. Louis, MO (US); Marc D. Feldman, San Antonio, TX (US); Thomas E. Milner, Austin, TX (US); JeeHyun Kim, Austin, TX (US); Gregory L. Freeman, San Antonio, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 1345 days.

(21) Appl. No.: 10/500,577

(22) PCT Filed: Jan. 15, 2003

(86) PCT No.: PCT/US03/01135

§ 371 (c)(1),
(2), (4) Date: Dec. 27, 2004

(87) PCT Pub. No.: WO03/059162

PCT Pub. Date: Jul. 24, 2003

(65) Prior Publication Data

US 2005/0113678 A1 May 26, 2005

Related U.S. Application Data

(60) Provisional application No. 60/348,604, filed on Jan. 15, 2002.

(51) Int. Cl.
*A61B 6/00* (2006.01)
*A61B 5/05* (2006.01)
(52) U.S. Cl. .................. 600/473; 600/476

(58) Field of Classification Search ......... 600/462–463, 600/425, 467; 436/14, 16
See application file for complete search history.

(56) References Cited

U.S. PATENT DOCUMENTS

| | | | |
|---|---|---|---|
| 4,448,188 A * | 5/1984 | Loeb | 600/108 |
| 4,923,442 A * | 5/1990 | Segall et al. | 604/522 |
| 5,084,558 A | 1/1992 | Rausch et al. | 530/385 |
| 5,234,903 A | 8/1993 | Nho et al. | 514/6 |
| 5,296,465 A | 3/1994 | Rausch et al. | 514/6 |
| 5,321,501 A | 6/1994 | Swanson et al. | 356/345 |
| 5,352,773 A | 10/1994 | Kandler et al. | 530/385 |

(Continued)

OTHER PUBLICATIONS

Ali AA, Ali GS, Steinke JM, Shepherd AP. Co-oximetry interference by hemoglobin-based blood substitutes. Anesth Analg. 2001;92:863-869.*

(Continued)

*Primary Examiner*—Eric F Winakur
*Assistant Examiner*—Helene Bor
(74) *Attorney, Agent, or Firm*—J. Peter Paredes; Rosenbaum & Silvert, P.C.

(57) ABSTRACT

Disclosed are improved methods and compositions for use in light-based in vivo imaging and treatment. The techniques described involve the use of low-scattering, oxygen-carrying blood substitutes in imaging and treatment methods, including OCT imaging. The invention has particular advantages in imaging within the cardiovascular system and highly vascularized or oxygen-dependent tissues.

54 Claims, 2 Drawing Sheets

U.S. PATENT DOCUMENTS

| | | | |
|---|---|---|---|
| 5,403,575 A | 4/1995 | Kaufman et al. | 424/1.89 |
| 5,413,558 A | 5/1995 | Paradis | 604/101 |
| 5,459,570 A | 10/1995 | Swanson et al. | 356/345 |
| 5,465,147 A | 11/1995 | Swanson | 356/345 |
| 5,469,261 A | 11/1995 | Hellmuth et al. | 356/361 |
| 5,476,974 A | 12/1995 | Moore et al. | 568/677 |
| 5,491,524 A | 2/1996 | Hellmuth et al. | 351/212 |
| 5,493,109 A | 2/1996 | Wei et al. | 250/201.3 |
| 5,501,226 A | 3/1996 | Petersen et al. | 128/691 |
| 5,502,094 A | 3/1996 | Moore et al. | 524/145 |
| 5,506,634 A | 4/1996 | Wei et al. | 351/221 |
| 5,537,162 A | 7/1996 | Hellmuth et al. | 351/206 |
| 5,549,114 A | 8/1996 | Petersen et al. | 128/691 |
| 5,567,765 A | 10/1996 | Moore et al. | 524/801 |
| 5,589,189 A | 12/1996 | Moynihan | 424/450 |
| 5,618,919 A | 4/1997 | Rausch et al. | 530/385 |
| 5,644,642 A | 7/1997 | Kirschbaum | 382/103 |
| 5,691,452 A | 11/1997 | Gawryl et al. | 530/385 |
| 5,752,518 A | 5/1998 | McGee et al. | 128/662.06 |
| 5,753,616 A | 5/1998 | Rausch et al. | 514/6 |
| 5,785,950 A | 7/1998 | Kaufman et al. | 424/1.89 |
| 5,795,295 A | 8/1998 | Hellmuth et al. | 600/407 |
| 5,830,133 A | 11/1998 | Osten et al. | 600/322 |
| 5,848,969 A | 12/1998 | Panescu et al. | 600/462 |
| 5,904,651 A | 5/1999 | Swanson et al. | 600/407 |
| 5,905,141 A | 5/1999 | Rausch et al. | 530/385 |
| 5,908,445 A | 6/1999 | Whayne et al. | 607/122 |
| 5,929,031 A | 7/1999 | Kerwin et al. | 514/12 |
| 5,955,581 A | 9/1999 | Rausch et al. | 530/385 |
| 5,956,355 A | 9/1999 | Swanson et al. | 372/20 |
| 5,968,064 A | 10/1999 | Selmon et al. | 606/189 |
| 5,975,699 A | 11/1999 | Hellmuth | 351/211 |
| 5,985,332 A | 11/1999 | Barnikol et al. | 424/529 |
| 5,991,697 A | 11/1999 | Nelson et al. | 702/49 |
| 5,994,509 A | 11/1999 | Barnikol | 530/385 |
| 5,994,690 A | 11/1999 | Kulkarni et al. | 250/216 |
| 6,002,480 A | 12/1999 | Izatt et al. | 356/345 |
| 6,004,314 A | 12/1999 | Wei et al. | 606/12 |
| 6,006,128 A | 12/1999 | Izatt et al. | 600/476 |
| 6,010,449 A | 1/2000 | Selmon et al. | 600/117 |
| 6,037,579 A | 3/2000 | Chan et al. | 250/216 |
| 6,047,218 A | 4/2000 | Whayne et al. | 607/122 |
| 6,053,613 A | 4/2000 | Wei et al. | 351/205 |
| 6,111,645 A | 8/2000 | Tearney et al. | 356/354 |
| 6,120,516 A | 9/2000 | Selmon et al. | 606/159 |
| 6,134,003 A | 10/2000 | Tearney et al. | 356/345 |
| 6,159,445 A | 12/2000 | Klaveness et al. | 424/9.6 |
| 6,160,826 A | 12/2000 | Swanson et al. | 372/20 |
| 6,191,862 B1 | 2/2001 | Swanson et al. | 356/450 |
| 6,201,608 B1 | 3/2001 | Mandella et al. | 356/491 |
| 6,208,415 B1 | 3/2001 | De Boer et al. | 356/351 |
| 6,217,527 B1 | 4/2001 | Selmon et al. | 600/585 |
| 6,219,575 B1 | 4/2001 | Nemati | 604/20 |
| 6,221,049 B1 | 4/2001 | Selmon et al. | 604/164.13 |
| 6,231,546 B1 | 5/2001 | Milo et al. | 604/164.13 |
| 6,233,055 B1 | 5/2001 | Mandella et al. | 356/479 |
| 6,252,666 B1 | 6/2001 | Mandella et al. | 356/479 |
| 6,275,726 B1 | 8/2001 | Chan et al. | 600/476 |
| 7,291,592 B2 * | 11/2007 | Gould et al. | 514/6 |

OTHER PUBLICATIONS

Rameshraja Palaparthy, Huashan Wang, Anil Gulati, Current aspects in pharmacology of modified hemoglobins, Advanced Drug Delivery Reviews. vol. 40, Issue 3, Blood Substitutes, Feb. 28, 2000, pp. 185-198.*

BioPure Material Safety Data Sheet. http://bayervet.compassites.com/viewfile.php?c=5290001&t=pdf Accessed Nov. 9, 2008.*

Brezinski et al., "Imaging of Coronary Artery Microstructure (In Vitro) with Optical Coherence Tomography," *Am. J. Cardiology*, 77:92-93, 1996.

Brezinski et al., "Index Matching to Improve Optical Coherence Tomography Imaging Through Blood," *Circulation*, 103:1999-2003, 2001.

Cassis and Lodder, "Near-IR Imaging of Atheromas in Living Arterial Tissue," *Anal. Chem.*, 65:1247-1256, 1993.

Chen et al., "Noninvasive Imaging of In Vivo, Blood Flow Velocity Using Optical Doppler Tomography," *Optics Letters*, 22(14):1119-1121, 1997.

Feldman et al., "Use of a Blood Substitute to determine Instantaneous Murine Right Ventricular Thickening with Optical Coherence Tomography," *J. Am. College Cardiology*, 39(5 Supp. A):397A, Abstract #894-5, 2002.

Fishman et al., "In Vivo Measurements of Vascular Oxygen Tension in Tumors Using MRI of a Fluorinated Blood Substitute," *Investigative Radiology*, 24(1):65-71, 1989.

Geyer, "'Bloodless Rats' Through the Use of Artificial Blood Substitutes," *Federation Proc.*, 34:1499-1505, 1975.

Hodakowski et al., "Ultra-Pure Polymerized Bovine Hemoglobin Blood Substitute: Effects on the Coronary Circulation," *Biomat. Art. Cells Immob. Biotech.*, 20(2-4):669-672, 1992.

Joseph et al., "Magnetic Resonance Imaging of Fluorine in Rats Infused with Artificial Blood," *Investigative Radiology*, 20(5):504-509, 1985.

Kim et al., "Murine Myocardium OCT Imaging with a Blood Substitute," *Proc. SPIE*, 4619:165-170, 2002.

Lee et al., "Limitations or the Efficacy of Hemoglobin-Based Oxygen-Carrying Solutions," *J. Appl. Physiol.*, 79(1):236-242, 1995.

Lok, "Blood Product From Cattle Wins Approval for Use in Humans," *Nature*, 410:855, 2001.

Moreira et al., "Effect of Hemopurer® on the Performance of Ektachem and Hitachi Clinical Analyzers," *Clin. Chem.*, 43(9):1790-1791, 1997.

Moreno et al., "Detection of Lipid Pool, Thin Fibrous Cap, and Inflammatory Cells in Human Aortic Atherosclerotic Plaques by Near-Infrared Spectroscopy," *Circulation*, 105:923-927, 2002.

Oxyglobin® Product Information.

Patwari et al., "Assessment of Coronary Plaque With Optical Coherence Tomography and High-Frequency Ultrasound," *Am. J. Cardiology*, 85:641-644, 2000.

Roggan et al., "Optical Properties of Circulating Human Blood in the Wavelength Range 400-2500 NM," *J. Biomed. Optics*, 4(1):36-46, 1999.

Saito et al., "Mycardial Contrast Echocardiography Using Artificial Blood (Fluosol-DA): A Comparison with Left Ventricular Wall Motion in the Experimental Ischemic Heart," *J. Cardiography*, 14(4):677-688, 1984.

Slanetz et al., "Hemoglobin Blood Substitutes in Extended Preoperative Autologous Blood Donation: An Experimental Study," *Surgery*, 115:246-254, 1994.

Spahn and Pasch, "Physiological Properties of Blood Substitutes," *News Physiol. Sci.*, 16:38-41, 2001.

Stowell et al., "Progress in the Development of RBC Substitutes," *Transfusion*, 41:287-299, 2001.

Villard et al., "Use of a Blood Substitute to Determine Instantaneous Murine Right Ventricular Thickening with Optical Coherence Tomography," *Circulation*, 105:1843-1849, 2002.

Villard Masters Thesis, "Use of a Blood Substitute to Determine Instantaneous Murine Ventricular Thickening with Optical Coherence Tomography," *The University of Texas at Austin*, submitted Aug. 2001; approved; and released between Jan. 2002 and Jul. 9, 2002.

Vlahakes et al., "Hemodynamic Effects and Oxygen Transport Properties of a New Blood Substitute in a Model of Massive Blood Replacement," *J. Thorac. Cardiovasc. Surg.*, 100:379-388, 1990.

International Search Report for PCT Application No. PCT/US03/01135, mailed May 16, 2003.

Tuchin, Valery V., et al., "Whole blood and RBC sedimentation and aggregation study using OCT", *Proc. SPIE*, 4263: 143-149 (2001).

Supplementary European Search Report, pp. 1-3 (Jan. 30, 2009).

* cited by examiner

METHODS AND COMPOSITIONS TO REDUCE SCATTERING OF LIGHT DURING THERAPEUTIC AND DIAGNOSTIC IMAGING PROCEDURES

The present application claims priority to U.S. provisional application Ser. No. 60/348,604, filed Jan. 15, 2002, the entire text and figures of which are incorporated herein by reference without disclaimer.

The U.S. Government owns rights in the present invention pursuant to grant numbers HL-59472 from the National Institutes of Health.

BACKGROUND OF THE INVENTION

1. Field of the Invention

The present invention relates most substantially to the field of in vivo imaging. The invention provides methods and compositions for use in improved light-based imaging and treatment modalities based upon the use of low-scattering, oxygen-carrying blood substitutes. The use of hemoglobin solutions in combination with OCT imaging is a particular example within the invention. The compositions, methods and uses of the invention have important advantages in imaging tissues that are intolerant of ischemia.

2. Description of Related Art

Non-invasive diagnostic imaging is now widely used in clinical practice. One of the commonly employed techniques is imaging with ultrasound, which measures the intensity of backscattered sound waves. However, ultrasound technology is limited both in the rate at which images can be generated and in the structural detail that can be provided. Thus, ultrasound is not best suited to in vivo imaging on a precise scale or in connection with rapidly moving biological tissues. Such drawbacks reduce the applications of ultrasound, e.g., limiting its use in cardiovascular imaging.

A promising new technique, optical coherence tomography (OCT), has been developed and proposed for use in certain aspects of in vivo imaging. OCT is analogous to ultrasound, but measures the intensity of backscattered light rather than sound waves. Since light travels faster than sound and has a substantially shorter wavelength, the use of OCT provides micron scale resolution (Huang et al., 1991) and faster-than-video imaging speeds (Rollins et al., 1998). The relative simplicity of the instrumentation also allows for inexpensive construction.

Early biomedical applications of OCT focused on imaging stationary and transparent tissues, such as the eye, where imaging depths can be deeper than 2 cm (Hee et al., 1995). Further developments have been applied to non-transparent tissues, such as skin, where structures as deep as 1-2 mm have been visualized (Schmitt et al., 1995). Dynamic, but nearly transparent, structures such as the developing in vivo tadpole heart, have also been studied using OCT (Boppart et al., 1997).

OCT has now been proposed for use in imaging other biological tissues, and there has recently been increasing interest in applying OCT to the cardiovascular system. In vivo intravascular imaging has been reported in rabbit aorta (Fujimoto et al., 1999), and in vitro studies with coronary arteries have suggested a method of determining fibrous cap thickness of atherosclerotic plaques (Brezinksi et al., 1996; Patwari et al., 2000). However, despite such proposals, the use of OCT has yet to prove satisfactory in many biological imaging applications.

The limitations of applying OCT to dynamic, non-transparent biological structures are particularly evident in attempts at cardiovascular imaging. Although optical Doppler tomography (ODT), which combines Doppler velocimetry with OCT, has been used to assess blood flow in the chick chorioallantoic membrane and in rodent skin, problems with signal attenuation were noted (Chen et al., 1997). Other reports have also indicated that potential in vivo applications of OCT imaging are complicated by the presence of blood in the imaging field, which results in substantial signal attenuation (Brezinski et al., 2001). Therefore, although cardiovascular imaging with light seemed to offer a solution to the drawbacks of ultrasound, practical applications have proven problematical due to significant optical attenuation.

In preliminary attempts at OCT intravascular imaging in the rabbit aorta, saline infusions were required to obtain adequately defined images (Fujimoto et al., 1999). Others have commented that the use of such saline flushes will likely need to be eliminated in order for intravascular OCT imaging to advance (Brezinski et al., 2001). The alternative approach proposed was to modify plasma to match the index of refraction to that of red blood cells, i.e., increasing the serum refractive index closer to that of the erythrocyte cytoplasm (Brezinski et al., 2001). However, whilst such "index matching" techniques have been pursued in relatively crude in vitro experiments using dextran and intravenous contrast agents, the in vitro tests have been less than convincing and the proposal has not been validated in acceptable in vivo models.

Therefore, despite attempts to refine or optimize existing imaging technology, there remains in the art a need for improved in vivo imaging techniques, particularly rapid techniques that provide high resolution. The development of improved techniques that can be effectively applied to imaging in the cardiovascular system, heart, brain and other blood-rich tissues is particularly desirable. In trying to expand the use of in vivo OCT imaging into such important fields, it would be important to overcome the existing need for saline flushes, which currently limits OCT applications in such areas. Accordingly, the ability to rapidly provide high resolution images of blood-rich tissues without causing ischemic tissue damage would represent a particularly significant advance.

SUMMARY OF THE INVENTION

The present invention solves such needs in the art by providing a range of improved imaging methods with important applications in imaging through blood-rich structures. The invention particularly provides improved light-based imaging and treatment methods, including OCT imaging, using low-scattering, oxygen-carrying blood substitutes, such as hemoglobin solutions. The surprising use of the invention significantly reduces signal attenuation due to scattering from blood without resorting to the limitations of saline flushes. The invention thus simultaneously reduces scattering and significantly improves image quality whilst maintaining tissue oxygenation, avoiding ischemia and related tissue damage. The methods, compositions, kits and uses of the invention are therefore ideal for rapid and high resolution imaging of cardiovascular, brain and other highly vascularized tissues.

The inventors appreciated that the significant optical attenuation observed in light imaging techniques to date was mainly due to the scattering properties of erythrocytes. Initial proposals to limit signal attenuation concerned diluting blood with saline. More recent approaches suggested index matching, such as by diluting plasma with dextran or intravenous contrast agents. Whether using saline, dextran or another contrast agent, the inventors realized that the attendant reduction in oxygen carrying ability would severely limit any clinical imaging applications, and would essentially prevent imaging in organs and tissues that are largely intolerant to ischemia, such as the heart and brain.

Therefore, the inventors intended to develop an alternative approach, leading to the present invention's use of oxygen-carrying blood substitutes to lower the hematocrit and minimize scattering. In turning from the field of imaging technology to that blood substitutes, the inventors realized that despite the extensive volume of documentation on the chemical, biological and physiological properties of various blood substitutes, there was no meaningful information on the optical properties any of these materials.

From their own analyses and studies, the inventors were able to select blood substitutes with appropriate low-scattering optical properties and sufficient oxygen carrying, biological and physiological properties, thus arriving at the present invention. The preferred low-scattering blood substitutes for use in the invention are hemoglobin solutions. The inventors also determined that the perfluorocarbon (PFC) blood substitutes prominent in the literature were essentially unsuitable for use in the present invention, as rather than having low-scattering optical properties, they would exhibit essentially the same problematical scattering as whole blood.

The invention thus provides a range of improved methods for performing optical imaging and light-based treatment procedures in which the blood associated with the tissue is perfused with a biologically effective amount of a low-scattering, oxygen-carrying blood substitute. The surprising use of low-scattering blood substitutes, such as non-particulate, hemoglobin-based solutions, provides dual benefits, both from the biochemical properties of oxygen carriage and the advantageous optical transparency at far red and near infrared wavelengths. By sufficiently reducing the hematocrit with such a low-scattering, oxygen-carrying blood substitute, in vivo imaging can now be conducted in heart, brain and other blood-rich structures.

Proof of principle of the invention is provided by the present data, quantifying the regional right ventricular function in the intact beating murine heart using OCT imaging in combination with an artificial hemoglobin solution. From this validation, the invention now provides for the advantageous use of low-scattering, oxygen-carrying blood substitutes in various therapeutic and diagnostic imaging embodiments, where reduced light scattering is beneficial.

In overcoming the limitations and prejudices in the prior art in the successful development of blood substitutes for use in improved imaging, the inventors discovered a window of properties for effective blood substitutes, within which scattering is substantially reduced, but oxygen-carrying capacity is not substantially impaired. Compositions and methods that operate within the window defined by the invention can now be successfully applied in a range of therapeutic and diagnostic embodiments, as will be known to those of ordinary skill in the art in light of the present disclosure.

As used throughout the entire application, the terms "a" and "an" are used in the sense that they mean "at least one", "at least a first", "one or more" or "a plurality" of the referenced components, except in instances wherein an upper limit is thereafter specifically stated or would be clearly understood by those of ordinary skill in the art. The operable limits and parameters of combinations, as with the amounts of any single agent, will be known to those of ordinary skill in the art in light of the present disclosure. The "a" and "an" terms are also used to mean "at least one", "at least a first", "one or more" or "a plurality" of steps in the recited methods, except where specifically stated.

Throughout the present specification and claims, the term "or" is used in the sense that it means "and/or" in reference to the disclosed and claimed components and steps, except in instances wherein a different meaning is thereafter specifically stated or would be clearly understood by one of ordinary skill in the art. Thus, unless otherwise expressly stated or clearly known by those of ordinary skill in the art, the term "or" is simply used as a succinct reference term to cover each recited component or step and all combinations thereof.

In a general and overall sense, the invention provides methods for performing optical imaging or treatment of at least a first tissue, or a tissue, in an animal or human, comprising providing into the blood associated with at least a first tissue, or a tissue, a biologically effective amount of a low-scattering, oxygen-carrying blood substitute, and applying an optical imaging or treatment step to the at least a first tissue or tissue.

The invention may thus also be described as providing a low-scattering, oxygen-carrying blood substitute for use in an optical imaging or treatment method, i.e., for use in a clinical or veterinary optical imaging or treatment method.

Further, the invention provides the use of a low-scattering, oxygen-carrying blood substitute in the manufacture of a medicament for use in an optical imaging or treatment method, i.e., for use in a clinical or veterinary optical imaging or treatment method.

Advantageous methods and uses of the invention therefore provide means for performing optical imaging or treatment of a tissue in an animal or human that comprises a substantial blood fraction, which methods and uses comprise:

(a) introducing into the blood fraction of the tissue an amount of a low-scattering, oxygen-carrying blood substitute effective to substantially or significantly reduce optical scattering from the blood fraction whilst substantially or effectively maintaining oxygenation in the tissue; and (b) applying an optical imaging or treatment step to the tissue.

The present invention may also be described as methods and uses for performing optical imaging and treatment of blood-containing or blood-rich tissues in animals and humans in the absence of a saline flush. Further, this invention may be described as methods and uses for performing optical imaging and treatment of blood-containing or blood-rich tissues in animals and humans in the absence of a perfluorocarbon blood substitute. Accordingly, the invention provides methods and uses for optical imaging and treatment of blood-containing or blood-rich tissues in animals and humans using oxygen-carrying blood substitutes that both substantially maintain tissue oxygenation and substantially reduce scattering.

In terms of imaging, the invention provides methods and uses for performing optical imaging of at least a first tissue, or a tissue, in an animal or human, comprising providing into the blood associated with the at least a first tissue, or a tissue, a biologically effective amount of a low-scattering, oxygen-carrying blood substitute, and applying an optical imaging step to the at least a first tissue or tissue.

The imaging methods and uses of the invention may further be described as those for generating an image of at least a first vascularized tissue by in vivo diagnostic light imaging, comprising providing into the blood perfusing the vascularized tissue a biologically effective amount of a low-scattering, oxygen-carrying blood substitute, and executing a diagnostic light imaging technique to generate an image of the vascularized tissue.

In therapeutic embodiments, the invention provides methods and uses for executing a therapeutic or treatment step in at least a first tissue, or a tissue, in an animal or human, comprising providing into the blood associated with the at least a first tissue, or a tissue, a biologically effective amount of a low-scattering, oxygen-carrying blood substitute, and applying an optical therapeutic or treatment step to the at least a first tissue or tissue.

Whether in imaging or therapy, the low-scattering, oxygen-carrying blood substitute is typically a solution comprising at least a first oxygen carrier. A "solution comprising at least a first oxygen carrier", as used herein, is an oxygen-carrying solution effective to reduce, and preferably to substantially reduce, optical scattering when mixed with blood or whole blood. Such properties can be effectively determined in vitro, as disclosed herein. However, in the practice of the invention, the low-scattering, oxygen-carrying blood substitutes are preferably defined as solutions comprising at least a first oxygen carrier that are effective to reduce, and preferably to substantially reduce, optical scattering from a blood fraction during in vivo imaging or therapy.

Low-scattering, oxygen-carrying blood substitute solutions comprising at least a first oxygen carrier will preferably not contain substantial amounts of particles approximating to the size of an erythrocyte. Preferably, the largest particles or species in the low-scattering, oxygen-carrying blood substitute solutions will have a size of less than about 800 nanometers (nm), and more preferably, a size of less than about 80 nm. In certain preferred embodiments, the largest particles or species in the low-scattering, oxygen-carrying solutions for use in the invention will have a size of less than about 70 nm, 60 nm, 50 nm, 40 nm, 30 nm or 20 nm, and more preferably, a size of between about 10 nm and about 5 nm.

The low-scattering, oxygen-carrying blood substitute is also preferably a solution comprising at least a first oxygen carrier, in which the refractive index of the at least a first oxygen carrier is substantially equal to other molecular species in the solution.

Preferred "low-scattering, oxygen-carrying blood substitutes" are substantially non-particulate hemoglobin solutions, more preferably substantially non-particulate, homogeneous, acellular hemoglobin solutions. The preferred use of "acellular" hemoglobin solutions avoids particle sizes in the 8 μm range of the erythrocyte. Preferably, the largest species in the solution is hemoglobin, with a size of about 6 nanometers.

Such hemoglobin solutions may comprise bovine, porcine, ovine or primate hemoglobin, with primate hemoglobin being preferred and human hemoglobin being more preferred. Mixtures of hemoglobins may be included. The substantially non-particulate hemoglobin solutions and substantially non-particulate, homogeneous, acellular hemoglobin solutions may comprise recombinantly produced hemoglobin. Suitable hemoglobin solutions may also or alternatively comprise crosslinked hemoglobin or polymerized hemoglobin. Particular examples for use in the invention are hemoglobin solutions comprising glutaraldehyde crosslinked, polymerized hemoglobins. Surface modified hemoglobins may also be employed in the methods and uses of the invention.

The low-scattering, oxygen-carrying blood substitute is selected so that it is "effective to substantially reduce optical scattering from the blood fraction whilst substantially or effectively maintaining tissue oxygenation". The blood substitute should thus have "a sufficient or effective oxygen carrying capacity", i.e., an oxygen carrying capacity sufficient or effective to substantially maintain tissue function during the imaging or therapeutic method, and/or sufficient or effective to permit substantial restoration of tissue function after cessation of the imaging or therapeutic method. The blood substitute should thus have an "oxygen carrying capacity sufficient to substantially maintain or restore tissue function for the chosen imaging or therapeutic procedure".

An "oxygen-carrying capacity sufficient for the selected imaging or therapeutic embodiment" means that the low-scattering, oxygen-carrying blood substitute, preferably the substantially non-particulate hemoglobin solution, should maintain sufficient tissue oxygenation to substantially or significantly reduce ischemia and related tissue damage in comparison to the use of the same imaging or therapeutic embodiment when used in conjunction with a saline flush. Preferably, the "sufficient oxygen-carrying capacity" will be effective to maintain tissue oxygenation at levels sufficient to substantially avoid ischemia and related tissue damage.

Low-scattering, oxygen-carrying blood substitutes with low oxygen carrying capacities, as compared to whole blood, will be more suitable for use in imaging and therapeutic embodiments of lesser duration and/or in connection with tissues that are more tolerant to ischemia. Low-scattering, oxygen-carrying blood substitutes with moderate or high oxygen carrying capacities are preferred, and those with high oxygen carrying capacities are more preferred, particularly for use in imaging and therapeutic embodiments of longer duration and/or for use in tissues that are less tolerant to ischemia and more prone to resultant tissue damage, such as heart and brain. A low-scattering, oxygen-carrying blood substitute with "a high oxygen carrying capacity", as defined herein, is a blood substitute that has at least about 70% of the oxygen carrying capacity of whole blood.

Accounting for the tissue, and the nature and duration of the chosen imaging or therapeutic procedure, the low-scattering, oxygen-carrying blood substitute has an oxygen carrying capacity prior to administration of at least about 99%, 98%, 97%, 96%, 95%, 94%, 93%, 92%, 91% or about 90% of the oxygen carrying capacity of whole blood; preferably, has an oxygen carrying capacity prior to administration of at least about 89%, 88%, 87%, 86%, 85%, 84%, 83%, 82%, 81% or about 80% of the oxygen carrying capacity of whole blood; and more preferably, has an oxygen carrying capacity prior to administration of about 79%, 78%, 77%, 76%, 75%, 74%, 73%, 72%, 71% or about 70% of the oxygen carrying capacity of whole blood.

However, such values are not limiting on the invention, in which the low-scattering, oxygen-carrying blood substitute may have an oxygen carrying capacity prior to administration of about 69%, 68%, 67%, 66%, 65%, 64%, 63%, 62%, 61% or about 60% of the oxygen carrying capacity of whole blood; or of about 59%, 58%, 57%, 56%, 55%, 54%, 53%, 52%, 51% or about 50% of the oxygen carrying capacity of whole blood; or of about 49%, 48%, 47%, 46%, 45%, 44%, 43%, 42%, 41% or about 40% of the oxygen carrying capacity of whole blood; or of about 39%, 38%, 37%, 36%, 35%, 34%, 33%, 32%, 31% or about 30% of the oxygen carrying capacity of whole blood; or of about 29%, 28%, 27%, 26%, 25%, 24%, 23%, 22%, 21% or about 20% of the oxygen carrying capacity of whole blood; or even of about 19%, 18%, 17%, 16%, 15%, 14%, 13%, 12%, 11% or about 10% of the oxygen carrying capacity of whole blood or less, so long as the oxygen-carrying capacity is sufficient for the chosen embodiment.

Any ranges between any of the foregoing values are included, such as oxygen carrying capacities prior to administration of between about 60% and about 99%, preferably, between about 65% and about 90%, and more preferably, between about 70% and about 80% of the oxygen carrying capacity of whole blood.

Where hemoglobin solutions are used, the hemoglobin solution should be selected so that it is also effective to substantially reduce optical scattering from the blood fraction whilst substantially or effectively maintaining tissue oxygenation. Again depending on the tissue, nature and duration of the procedure, the hemoglobin solution prior to administration may have a hemoglobin concentration of at least about 99%, 98%, 97%, 96%, 95%, 94%, 93%, 92%, 91% or about 90% of the hemoglobin concentration of whole blood; preferably, will have a hemoglobin concentration of at least about 89%, 88%, 87%, 86%, 85%, 84%, 83%, 82%, 81% or about 80% of the hemoglobin concentration of whole blood; and more preferably, will have a hemoglobin concentration of about 79%, 78%, 77%, 76%, 75%, 74%, 73%, 72%, 71% or about 70% of the hemoglobin concentration of whole blood.

However, such values are not limiting on the invention, in which the hemoglobin solutions as measured prior to administration may have a hemoglobin concentration of about 69%, 68%, 67%, 66%, 65%, 64%, 63%, 62%, 61% or about 60% of the hemoglobin concentration of whole blood; or of about 59%, 58%, 57%, 56%, 55%, 54%, 53%, 52%, 51% or about 50% of the hemoglobin concentration of whole blood; or of about 49%, 48%, 47%, 46%, 45%, 44%, 43%, 42%, 41% or about 40% of the hemoglobin concentration of whole blood; or of about 39%, 38%, 37%, 36%, 35%, 34%, 33%, 32%, 31% or about 30% of the hemoglobin concentration of whole blood; or of about 29%, 28%, 27%, 26%, 25%, 24%, 23%, 22%, 21% or about 20% of the hemoglobin concentration of whole blood; or even of about 19%, 18%, 17%, 16%, 15%, 14%, 13%, 12%, 11% or about 10% of the hemoglobin concentration of whole blood or less, given that the oxygen-carrying capacity is sufficient for the chosen embodiment.

Any ranges between any of the foregoing values are included, such as hemoglobin concentrations prior to administration of between about 60% and about 99%, preferably, between about 65% and about 90%, and more preferably, between about 70% and about 80% of the hemoglobin concentration of whole blood.

In the practice of the invention, the low-scattering, oxygen-carrying blood substitute, preferably the substantially non-particulate hemoglobin solution, will be selected so that the provision of the blood substitute reduces the hematocrit of the blood associated with the tissue at least to about 35% or about 30% or less (as opposed to the hematocrit of whole blood, which is about 45%). Although more significant reductions in hematocrit are preferred, these moderate reductions in hematocrit are useful aspects of the invention, particularly in selected imaging and therapeutic embodiments, such as imaging through thinner barriers and in tissues with moderate or low blood content.

Preferably, however, the low-scattering, oxygen-carrying blood substitute or substantially non-particulate hemoglobin solution will be chosen so that the provision of the blood substitute reduces the hematocrit of the blood associated with the tissue at least to about 25%, 24%, 23%, 22%, 21% or about 20%; or preferably, reduces the hematocrit of the blood associated with the tissue at least to about 19%, 18%, 17%, 16%, 15%, 14%, 13%, 12%, 11% or about 10%; or more preferably, reduces the hematocrit of the blood associated with the tissue at least to about 9%, 8%, 7%, 6%, 5%, 4%, 3%, 2% or about 1% or even to 0%. Any ranges between any of the foregoing values are included, such as between about 0 and about 10%, preferably, between about 1% and about 10%, and more preferably, between about 1% and about 5%.

The "low-scattering" or "low optical scattering" properties of the oxygen-carrying blood substitute or substantially non-particulate hemoglobin solution for use in the invention are such that the blood substitute is "effective to reduce, and preferably to substantially reduce, optical scattering from blood", i.e., in admixture with blood or whole blood. During in vivo imaging or therapy, the selected blood substitute or hemoglobin solution will reduce, and preferably substantially or significantly reduce, optical scattering from the blood fraction associated with the tissue.

The ability to "reduce, substantially reduce or significantly reduce optical scattering from a blood fraction associated with a tissue" means that the use of the blood substitute or hemoglobin solution according to the invention reduces, substantially reduces or significantly reduces optical scattering during optical imaging or treatment in comparison to the optical scattering that occurs when the same imaging or therapeutic method is performed in conjunction with whole blood, i.e., when the blood of the animal or human is not substantially altered or perfused with another substance prior to or during the imaging or therapeutic method.

Depending on the quality of image or effectiveness of therapy prior to the present invention, a minimal or moderate reduction in optical scattering may still provide a beneficial or even significant improvement in the overall effectiveness of the imaging or therapeutic method. Any reduction in optical scattering that results in a reproducible improvement in the effectiveness of the imaging or therapeutic method is an "effective reduction in optical scattering" as used herein. Preferably, use of the invention will reduce, substantially reduce or significantly reduce optical scattering, such that there is a moderate, or preferably a significant, improvement in the effectiveness of the imaging or therapeutic method in comparison to the effectiveness when the same imaging or therapeutic method is performed in conjunction with whole blood.

Effective in vitro means to determine or confirm the ability of an oxygen-carrying blood substitute or substantially non-particulate hemoglobin solution to reduce, and preferably to substantially reduce, optical scattering from blood are available. Following in vitro studies, the in vivo low-scattering properties of the chosen blood substitute or hemoglobin solution can be quantitated during imaging or therapy in accepted animal models prior to clinical or veterinary use.

In a similar manner to the hematocrit reductions, although substantial reductions in scattering coefficient are preferred, moderate reductions in scattering coefficient are also useful in certain embodiments of the invention, particularly in imaging and therapeutic embodiments with thinner biological barriers and in tissues with moderate or low blood content. Suitable blood substitutes or hemoglobin solutions therefore include those that, when provided to an animal or human, reduce the hematocrit of the blood associated with the tissue to an amount effective to result in a scattering coefficient of about two thirds the scattering coefficient for whole blood or less.

In certain preferred embodiments, the blood substitute or hemoglobin solution is selected such that the provision of the low-scattering, oxygen-carrying blood substitute reduces the hematocrit of the blood associated with the tissue to an amount effective to result in a scattering coefficient of about one half the scattering coefficient for whole blood or less. The provision of the preferred low-scattering, oxygen-carrying blood substitutes may be defined as reducing the hematocrit of the blood associated with the tissue to an amount effective to result in a half maximal or lower scattering coefficient, as shown in FIG. 1B.

In other preferred embodiments, the blood substitute or hemoglobin solution is selected such that the provision of the low-scattering, oxygen-carrying blood substitute reduces the hematocrit of the blood associated with the tissue to an amount effective to result in a scattering coefficient of about one tenth the scattering coefficient for whole blood or less.

The decrease in scattering coefficient may also be defined using any particular value in this range. Accordingly, provision of the low-scattering, oxygen-carrying blood substitute can reduce the hematocrit of the blood associated with the tissue to an amount effective to result in a scattering coefficient of about 66%, 65%, 64%, 63%, 62%, 61%, 60%, 59%, 58%, 57%, 56%, 55%, 54%, 53%, 52%, 51% or about 50% of the scattering coefficient for whole blood; or preferably, of about 49%, 48%, 47%, 46%, 45%, 44%, 43%, 42%, 41% or about 40% of the scattering coefficient for whole blood; or more preferably, of about 39%, 38%, 37%, 36%, 35%, 34%, 33%, 32%, 31% or about 30% of the scattering coefficient for whole blood; or yet more preferably, of about 29%, 28%, 27%, 26%, 25%, 24%, 23%, 22%, 21% or about 20% of the scattering coefficient for whole blood; or most preferably, of about 19%, 18%, 17%, 16%, 15%, 14%, 13%, 12%, 11%, 10%, 9%, 8%, 7%, 6% or about 5% of the scattering coefficient for whole blood.

In terms of the decrease in scattering coefficient, this should preferably be assessed in the context of a particular wavelength. Accordingly, provision of the low-scattering, oxygen-carrying blood substitute is effective to reduce the scattering coefficient of the blood associated with the tissue to about two thirds, preferably to about one half, and more preferably, to about one tenth of the scattering coefficient of whole blood or less at a sample wavelength of between about 600 nm and about 1500 nm.

More preferably, provision of the low-scattering, oxygen-carrying blood substitute is effective to reduce the scattering coefficient of the blood associated with the tissue to about two thirds, preferably to about one half, and more preferably, to about one tenth of the scattering coefficient of whole blood or less at a sample wavelength of about 600 nm.

Provision of the low-scattering, oxygen-carrying blood substitute is thus effective to reduce the scattering coefficient of the blood associated with the tissue to about 50%, 49%, 48%, 47%, 46%, 45%, 44%, 43%, 42%, 41% or about 40% of the scattering coefficient for whole blood; or more preferably, to about 39%, 38%, 37%, 36%, 35%, 34%, 33%, 32%, 31% or about 30% of the scattering coefficient for whole blood; or yet more preferably, to about 29%, 28%, 27%, 26%, 25%, 24%, 23%, 22%, 21% or about 20% of the scattering coefficient for whole blood; or most preferably, to about 19%, 18%, 17%, 16%, 15%, 14%, 13%, 12%, 11% or about 10% of the scattering coefficient of whole blood or less at a sample wavelength of between about 600 nm and about 1500 nm, and more preferably, at a sample wavelength of about 600 nm.

In other preferred embodiments, provision of the low-scattering, oxygen-carrying blood substitute is defined as decreasing the scattering coefficient of the blood associated with the tissue to a scattering coefficient of about 0.4 $mm^{-1}$ or about 0.3 $mm^{-1}$ or less at about 1310 nm. More preferably, provision of the low-scattering, oxygen-carrying blood substitute decreases the scattering coefficient of the blood associated with the tissue to a scattering coefficient of about 0.2 $mm^{-1}$ at about 1310 nm.

The methods and uses of the present invention are widely applicable to a range of optical imaging and treatment methods, preferably those wherein the optical imaging or treatment step applies light of a wavelength of between about 600 nm and about 1500 nm.

Within the optical imaging field, the invention is suitable for use with one or more optical imaging steps that generate an image by light transmitting through at least a first tissue, and by light reflected by at least a first tissue. The optical imaging may also comprise a light refraction step.

The one or more optical imaging steps that can be improved by use of the invention thus include spectroscopic imaging steps, such as reflectance spectroscopy, fluorescence spectroscopy, resonance spectroscopy and Raman spectroscopy.

The invention may also be used with one or more photoacoustic imaging steps, non-linear harmonic imaging steps and photothermal imaging steps.

The one or more optical imaging steps can provide a spatial image of the tissue, or a temporal image of the tissue.

One of the preferred uses of the invention is in connection with an optical coherence tomography (OCT) imaging step. In certain preferred embodiments, the invention provides methods and uses for optical coherence tomography imaging of at least a first tissue in an animal or human, comprising providing into the blood associated with the at least a first tissue a biologically effective amount of a substantially non-particulate hemoglobin solution, and performing optical coherence tomography imaging of the at least a first tissue.

In other preferred embodiments, the invention provides methods and uses for optical coherence tomography imaging of a tissue in an animal or human that comprises a substantial blood fraction, i.e., "a blood-rich tissue". These methods and uses preferably comprise:

(a) introducing into the blood fraction of the tissue an amount of an essentially non-particulate hemoglobin solution effective to substantially reduce optical scattering from the blood fraction whilst substantially maintaining oxygenation in the tissue; and (b) performing optical coherence tomography imaging of the tissue.

Subsequent to, or in conjunction with, one or more imaging steps, the invention further provides for the execution of at least a first treatment or treatment step. The treatment or treatment step can be better selected from a number of candidate treatments or treatment steps, based upon the improved image provided by the optical imaging step of the invention. The imaging and treatment steps may each performed on the same tissue, or the treatment step may be performed on a distinct tissue that is functionally connected with the imaged tissue.

The one or more treatment or treatment steps may be performed shortly after the imaging step of the invention, such that treatment can be performed in the same general clinical procedure. Alternatively, the one or more treatment or treatment steps may be designed and subsequently performed in a different clinical procedure.

The at least a first treatment or treatment step selected after the one or more imaging steps of the invention may also be an optical treatment step, but it need not be. The one or more treatments or treatment steps may thus comprises surgical treatment steps, or the provision of therapeutic agents, or combinations thereof.

Aside from any imaging, the invention also provides for improved optical treatments and treatment steps. Exemplary optical treatment steps for use with the invention include laser ablation treatment, laser angioplasty treatment and laser photothermolyis treatment. The optical treatment step may also be a photoacoustic treatment step. The optical treatment step may comprise a light refraction step.

Whether imaging, treatment or combinations thereof, the invention is suitable for use with procedures to be performed in a variety of tissues and organs. For example, neural tissue, brain tissue and cardiac tissue. The invention may be used in connection with one or more tissues located within the kidney, lung, liver, spleen, brain, heart or one of the great vessels. The invention may also be used with imaging and/or treatment of an animal or human that has, or is at risk for developing, a vascularized tumor.

In both imaging and treatment, the at least a first tissue subject to the procedure may comprise at least two tissue layers, wherein at least a first of the tissue layers is associated with a substantial blood fraction. In many embodiments, the at least a first tissue subject to the procedure will comprise a plurality of tissue layers, wherein at least a first of the tissue layers is associated with a substantial blood fraction.

Although by no means limited to such embodiments, the invention has particular advantages in the imaging and/or treatment of highly perfused tissues and organs, such as cardiovascular tissue, cardiac tissue and blood vessels. The optical imaging or treatment step may be applied from the lumen of a blood vessel.

The invention is particularly suitable for imaging and/or treatment in embodiments wherein a blood vessel has, or is suspected to have, an atherosclerotic plaque or lesion. In related embodiments, the invention is also particularly suitable for imaging and/or treatment in connection with an animal or human that has, or is at risk for developing, a cardiac tissue or cardiac valve defect, or has suffered, or is at risk for developing, a heart attack.

Further advantageous methods and uses of the invention are in connection with imaging and/or treatment in an animal or human that has, or is at risk for developing, an ischemic tissue, particularly a life- or limb-threatening ischemia, particularly an animal or human that has suffered, or is at risk for developing, a stroke.

The invention is widely applicable for use in any of a wide range of animals, including all mammals, particularly humans, valuable or valued animals, such as racehorses and domestic pets, animals used to directly (e.g., meat) or indirectly (e.g., milk and eggs) produce food for human consumption, and animals preferred as models for pre-clinical studies. Imaging and treatment in humans are preferred embodiments of the invention, which may be effectively accomplished due to the oxygen-carrying capacity and lack of toxicity and side-effects of the administered solutions.

In addition to imaging and treatment in human adults and children, other exemplary embodiments of the invention include imaging and treatment in other primates; in horses, cows, pigs, boar, sheep, goat, buffalo, bison, llama, deer, elk, and other large animals; in dogs and cats; and in smaller animals, particularly those used as models for pre-clinical studies, such as mice, rats, guinea pigs, rabbits and the like, including genetically modified experimental animals.

Given that the low-scattering, oxygen-carrying blood substitutes for use in the invention provide notable advantages in tissue oxygenation, the present invention may be used for longer times than the prior art methods. In any event, the invention is evidently suitable for use in imaging and/or treatment protocols performed for a time at least as long as the standard times required in the art. The low-scattering, oxygen-carrying blood substitute may be provided to a blood vessel feeding the tissue from between about one or two minutes, or five or ten minutes, prior to applying the optical imaging or treatment step, up to a matter of hours before performing the optical imaging or treatment step.

The invention also further provides a number of kits comprising a low-scattering, oxygen-carrying blood substitute, such as those described above and herein, and instructions for using the blood substitute in an optical imaging or treatment method. The instructions may be written instructions, or computerized instructions, such as software associated with computer hardware.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
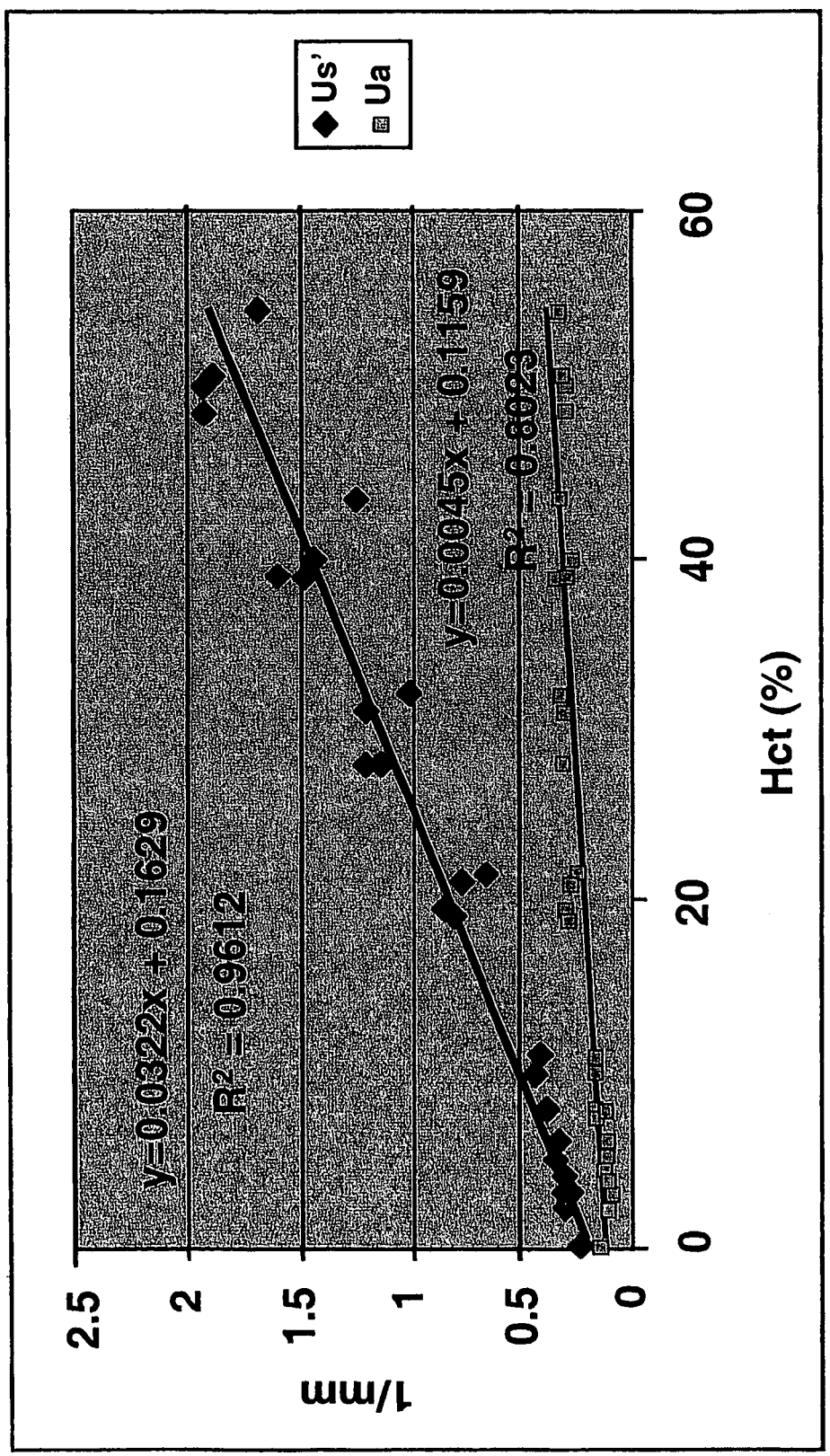
FIG. 1A. Optical properties of several dilutions of murine blood with Oxyglobin®. The reduced scattering coefficient ($\mu_s'$) is dependent upon the number of red blood cells per unit volume. The absorption coefficient ($\mu_a$) depends upon the concentration of hemoglobin.
Figure 1B:
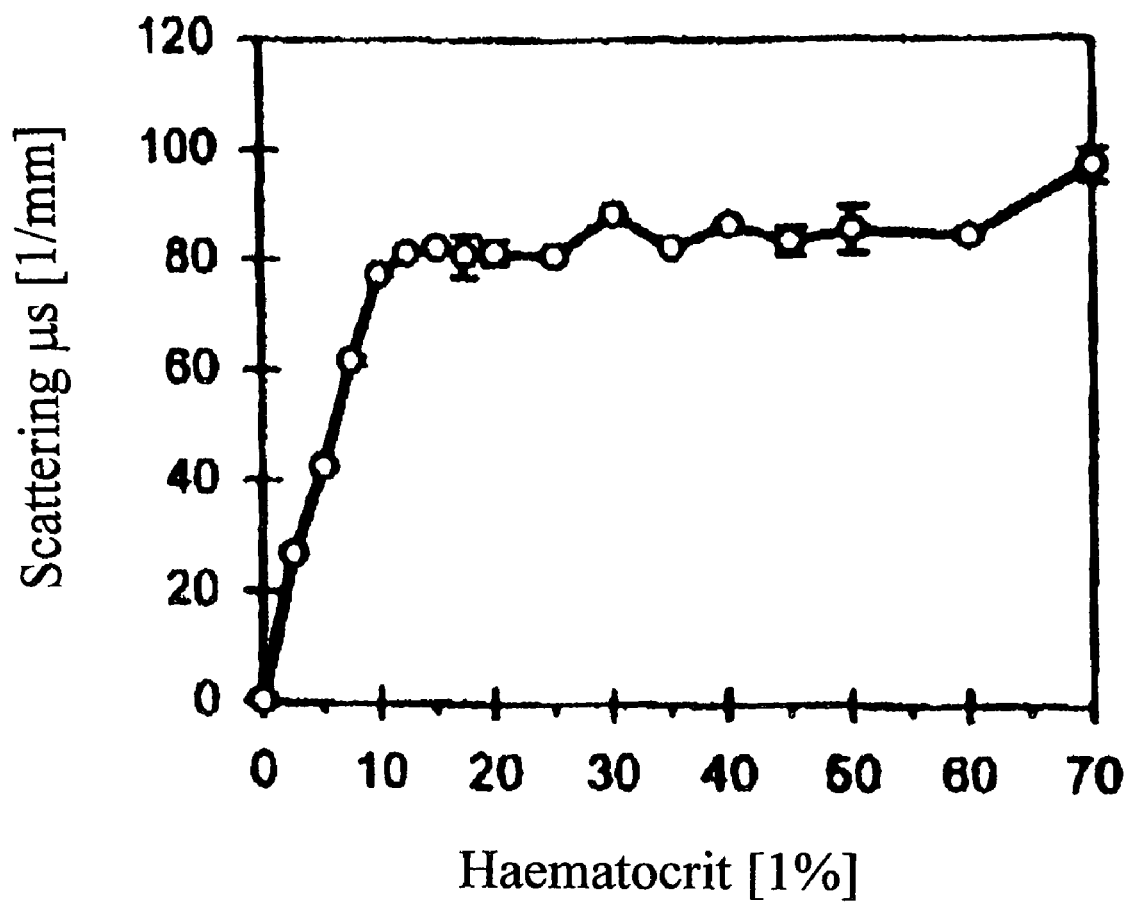
FIG. 1B. The scattering coefficient ($\mu_s$) of human blood as a function of hematocrit. Isotonic blood samples (300 mosmol/L) with a hematocrit ranging from 0 to 70% were measured at a wavelength of 633 nm. Mean values (n=3) are shown (taken from Roggan et al., 1999).

Techniques are needed to improve the resolution of imaging in biological tissues. Although OCT would have certain advantages, clinical applications of OCT appear limited due to substantial signal attenuation, believed to be due, in large part, to the presence of blood in the imaging field. In attempts to overcome such significant optical attenuation, researchers have diluted the blood in the imaging field with saline (Fujimoto et al., 1999).

Others have instead attempted to use "index matching" techniques, wherein dextran or an intravenous contrast agent is used. Using an in vitro system in which blood is pumped through transparent tubing, dilution with dextran or an intravenous contrast agent has been reported to reduce scattering somewhat (Brezinski et al., 2001). However, these authors indicated that neither of the compounds tested increased penetration sufficiently such that they could be used in vivo or at practical volumes (Brezinski et al., 2001).

U.S. Pat. No. 6,219,575, to Nemati, also concerns the objective of enhancing the optical transparency of a first biological tissue that is covered by a surface permeability barrier of a second tissue. The mechanism involves bypassing the barrier of the second tissue and delivering a clarifying agent to alter the attenuation characteristics of the biological tissue. U.S. Pat. No. 6,219,575 thus approaches the optical scattering problem very differently to the present invention. Nemati's use of clarifying agents (hypo- or hyper-osmotic agents) again signifies an index matching technique, as generally described in the foregoing Brezinski et al., 2001 article, although U.S. Pat. No. 6,219,575 also involves structural modification of the target tissue.

U.S. Pat. No. 6,159,445, to Klaveness et al., describes light imaging contrast agents and methods reported to increase light scattering by controlling particulate size and refractive index. U.S. Pat. No. 6,159,445, however, represents the opposite of the present invention, in that it concerns the use of solutions with increased scattering properties. In contrast, the present invention is based upon decreased scattering, which improves the penetration depth of light in the desired target.

In the context of the use of saline, dextran or other agents, the inventors realized that all such techniques were limited by a failure to address the oxygenation problem. Prior to the present invention, there had been no suggestion of how to reduce scattering during imaging techniques and yet compensate for the lack of oxygenation that results from dilution of the subject's blood. The inventors therefore realized that a new approach was needed so that imaging could be achieved without ischemia, thus opening up the imaging modalities to blood-filled and highly oxygen-dependent tissues.

In studying the existing problems with a view to developing improved in vivo imaging techniques, particularly those applicable to imaging in the cardiovascular system, blood-rich and/or more oxygen-dependent tissues, the inventors had to bridge various fields, including medical, physiological, biochemical and optical. Moreover, after studying the available literature, the inventors had to both apply existing knowledge in new and surprising ways, and had to extend the field of knowledge beyond what formerly existed, e.g., by analyzing particular physical properties of biological components for the first time.

In searching for a possible solution to the problem, the inventors first focused on the precise nature of the signal attenuation. Light attenuation in blood can originate from two sources: absorption by hemoglobin and scattering by red blood cells (Kramer et al., 1951; Twersky, 1970; Roggan et al., 1999; Steinke and Sheppard, 1986). As the significant source of light attenuation in whole blood is likely due to scattering, the inventors hypothesized that by diminishing the scattering properties of blood, the visualization of blood-containing structures, such as coronary arteries and ventricular myocardium, using optical imaging techniques would become feasible.

Although the scattering properties of blood could likely be reduced by removing or diluting the red blood cells, the inventors further realized that this would lead to oxygenation problems, ischemia and the associated and significant limitations. The inventors therefore decided to approach this problem by diluting the problematic red blood cells not with saline, but with an oxygen-carrying blood substitute, which was still able to reduce scattering. Despite the lack of previous information on the optical properties of blood substitutes, the inventors further discovered that substitutes based on acellular hemoglobin had the desired low-scattering optical properties, whilst substantially retaining the oxygen carrying capacity of natural blood. PFC-based blood substitutes, on the other hand, were determined to be unsuitable, as these emulsions do not have reduced scattering properties.

Although elegantly simple in hindsight, the present invention's surprising use of a low-scattering, oxygen-carrying blood substitute allows both problems in the prior art to be solved simultaneously. The methods devised, whereby blood is diluted with a substantially non-particulate, oxygen-carrying blood substitute, such as a hemoglobin solution, reduce scattering and maintain oxygenation.

The present examples report the reduced scattering observed when replacing murine blood with a hemoglobin-based blood substitute. The scattering and absorption properties of in vitro preparations of whole blood and dilutions of blood with a blood substitute were determined with a spectrophotometer and an inverse-adding doubling algorithm. OCT imaging of the same dilutions demonstrated a significant reduction in scattering at a hematocrit less than about 5%.

A fiber-optic OCT imaging system was used to image the murine right ventricular mid-free wall before and after isovolumic replacement with blood substitute. Strong light attenuation prevented full thickness imaging before replacement, while visualization of the full ventricular thickness was possible after replacement. Baseline and imaging hematocrits were 52.4±3.8% and 3.7±1.2%, respectively. End systolic and diastolic thickness values were 0.458±0.051 mm and 0.352±0.047 mm. Percent thickening fraction was 30.8±7.5%.

The present data therefore show that optical imaging of the intact beating murine right ventricle was substantially improved by isovolumic blood replacement with a hemoglobin-based blood substitute. By sufficiently reducing the hematocrit with a blood substitute to obtain significantly improved imaging whilst maintaining oxygenation, in the manner demonstrated herein, the present application therefore supports analogous applications of the invention in a range of optical diagnostic and therapeutic techniques, particularly those in cardiovascular medicine.

In an imaging device that uses light, light travels from a source to tissue, then from the tissue to a detector. The more signal that reaches the detector, the better the image. Signal can be prevented from reaching the detector, thus making a poorer image, by two mechanisms: absorption and scattering. If one considers light as numerous photons, then absorption can be thought of as a photon hitting a particle in the tissue and stopping there, dissipating its energy as heat. Scattering can be thought of as a photon "bouncing off" a particle in the tissue. When scattering and absorption are taken together, the result is "attenuation", or "extinction" ($\mu_{tot}=\mu_a+\mu_s$; where $\mu_{tot}$ is the total attenuation coefficient, $\mu_a$ is the absorption coefficient, and $\mu_s$ is the scattering coefficient).

The scattering phenomenon has a directional component, whereas absorption does not (because when a photon is scattered, it can travel in many different directions). Discounting the directional component of scattering, provides the reduced scattering coefficient, or $\mu_s'$, ($\mu_{tot}'=\mu_a+\mu_s'$). The reduced scattering coefficient can be easier to measure in certain practical embodiments, as described herein in Example 1.

The scattering properties of blood and blood substitutes are important in the present invention. Whole blood can be considered as a suspension of particles, i.e., cells in plasma. Red blood cells (erythrocytes) predominate, although white blood cells of numerous types (leukocytes) are also present. Important properties that affect the scattering coefficient are: index of refraction of the particle, e.g., red blood cell, the index of refraction of the suspending medium, e.g., plasma, the wavelength of light, the size of the particle, and the concentration of the particle.

A particularly important consideration for the present invention is the comparison between the wavelength of light and the particle size. To "see" a small particle (for example, in a microscope), light must be scattered off the particle so that the light does not enter the eye of the observer. In the present invention, the objective is to avoid scattering of light. The closer the wavelength is to the diameter of the particle, the more likely the light will scatter. In the case of blood, the particle, the red blood cell (if spherical), is about 8 μm in diameter. At the relevant wavelengths of 600 to 1500 μm, a light wave will encounter the particle several times on its path, and the light will likely scatter.

To overcome the existing scattering problems in the art, the present inventors realized that oxygen-carrying substitutes needed to be used in which any particles were either much smaller or much bigger than the red blood cell. The optical properties of acellular hemoglobin solutions were then determined experimentally by the inventors, for the first time, wherein they were found to be suitable to both reduce scattering and maintain oxygenation.

The largest particle in such artificial bloods is the hemoglobin molecule, which has a particle size of about 6 nm in diameter (as opposed to 8 μm for the red blood cell). As shown in Example 1, the inventors determined the reduced scattering coefficient of an acellular hemoglobin solution to be about 0.2 mm$^{-1}$ at a sample wavelength (1310 nm), whilst whole blood had a reduced scattering coefficient of about 1.8 mm$^{-1}$ at the same wavelength. This indicated to the inventors that such hemoglobin solutions had the properties required to reduce scattering sufficiently to provide meaningful benefit in imaging and light-based treatment modalities.

Within the field of artificial bloods, there has been substantial work in the area perfluorocarbons (PFCs). Indeed, several PFC products are available and have been used in humans. U.S. Pat. No. 5,403,575, No. 5,785,950 and No. 5,567,765 each generally concern PFC blood substitutes. Although "computed tomography" is mentioned in these patents, this relates to the use of multiple projections of X-rays to generate an image, and does not pertain to light imaging or OCT techniques.

In addition, there are preliminary scientific publications pertaining to the use of perfluorocarbon and fluorinated artificial blood emulsions. Joseph et al. (1995) and Fishman et al. (1999) each concern the use of perfluorocarbon emulsions in conjunction with MRI, whereas Saito et al. (1984) relates to myocardial contrast echocardiography using a fluorinated blood substitute (Fluosol-DA) as a contrast agent.

PFCs are characterized by a linear or cyclic carbon backbone that is highly substituted with fluorine and occasionally other halogens (Stowell et al., 2001; Spahn & Pasch, 2001). Pure PFCs are not miscible in water and are prepared for intravenous administration as suspensions or emulsions of the perfluorocarbon with a surfactant. These suspensions contain particles of about 200 nanometers in size. The inventors deduced that this was sufficiently close to the wavelengths of light contemplated for use in imaging and therapy, 600-1500 nm, that PFCs would likely also cause significant light scattering. Indeed, this was validated by the inventors' experimental studies, showing that the scattering properties of PFC blood substitutes are unsuitable for use in the present invention.

Therefore, in selecting a low-scattering, oxygen-carrying blood substitute for use in the present invention, those of ordinary skill in the art will now understand that a perfluorocarbon or PFC blood substitute should not be used. In contrast, the preferred compounds for use in the invention are cell-free hemoglobins. Although a range of suitable substantially non-particulate, homogeneous, acellular hemoglobin solutions can be prepared, either by purification or by recombinant expression, a number of commercial products are already available, which can be readily employed.

Exemplary products include PEG-Hb, a PEG-surface modified bovine hemoglobin (Enzon, Piscataway, N.J.) and PHP, pyridoxyl Hb polyoxyethylene, a pyridoxylated human hemoglobin to which polyoxyethylene is attached (Apex Bioscience, Research Triangle Park, N.C.).

"Crosslinked hemoglobins" are also available in which the hemoglobin subunits are covalently attached to form stabilized tetramers. Examples include "HemAssist", a chemically cross-linked human hemoglobin (Baxter Healthcare, Deerfield, Ill.), and Optro, a recombinantly expressed tetramer (Somatogen, Boulder, Colo., now Baxter).

Preferred hemoglobin solutions are those comprising polymerized hemoglobins. One suitable product is a glutaraldehyde-linked human hemoglobin available as PolyHeme (Northfield, Evanston, Ill.). Hemolink may also be used, which is a human hemoglobin crosslinked with open ring raffinose (Hemosol, Toronto).

One preferred example is the blood substitute termed Oxyglobin®. Oxyglobin® (Hemopure) has already been approved for human use in various countries, e.g., in the treatment of anemia. It has also been approved for veterinary use in the United States, e.g., for administration to anemic dogs.

Oxyglobin® is a glutaraldehyde-linked bovine hemoglobin, and is available from Biopure Corporation, 11 Hurley Street, Cambridge, Mass., 02141, U.S.A. Oxyglobin® is described in U.S. Pat. No. 5,691,452, No. 5,753,616, No. 5,955,581, No. 5,905,141, No. 5,618,919, No. 5,296,465 and No. 5,084,558. Aside from the commercial availability of Oxyglobin®, each of the foregoing U.S. patents are specifically incorporated herein by reference for the purposes of even further describing and enabling the preparation of Oxyglobin®.

In using any of such low-scattering, oxygen-carrying blood substitutes, tissue oxygenation during the procedure will not be a problem. Many of the blood substitutes have an oxygen carrying capacity that is substantially unreduced in comparison to whole blood. However, some reduction in oxygen carrying capacity can also be tolerated in certain circumstances, as monitored by a physician. For example, it is known in the art that some tissues can tolerate ischemia better than others. Moreover, the duration of the procedure can be monitored so any potential reduction in oxygen carrying capacity will not cause an adverse effect. In this regard, it is known that certain angioplasty techniques are already conducted in conjunction with a saline flush.

In regard to Oxyglobin®, this has a hemoglobin concentration of 13 g/dl, whereas normal hemoglobin has a concentration of 15 g/dl. Any potential reduction in oxygen carrying capacity of Oxyglobin® is shown in the present examples not to be problematic in myocardial imaging, as the inventors were able to image the full thickness of the ventricle.

Irrespective of the particular product or formulation chosen, the present invention provides for the use of low-scattering blood substitutes to effectively deliver oxygen while allowing optical imaging and therapy in the red and near infrared spectral range. The invention may be used in conjunction with a range of therapeutic and diagnostic procedures in which the interrogation of the target tissue would otherwise be obscured by blood.

This includes applications wherein the target tissue (e.g., to be imaged) is obscured by a whole blood barrier. For example, for an OCT probe inside the coronary artery, the target tissue to be imaged is the intima and other parts of the artery, and the barrier is whole blood. The present invention removes the scattering barrier by whole blood, but still allows delivery of oxygen. In general, one may be imaging through a sequence of tissue layers to a target layer. One or more of the intervening layers in the sequence may have a substantial blood fraction (1-100%) that effectively blocks imaging of the target layer due to attenuation by scattering. By perfusing those layers with a low-scattering, oxygen-carrying blood substitute, as in the present invention, such layers are kept oxygenated during the imaging of the targeted layer through the intervening layers. In some cases, the targeted layer may also contain blood (as in the ventricular imaging of the demonstration), in which case the addition of the low-scattering material allows imaging of that layer.

The invention thus provides for improvements in image quality or therapeutic effectiveness due to a reduction in scattering when replacing blood with a low-scattering substitute. In the imaging embodiments, it will now be possible to record depth-resolved images of atherosclerotic plaques. The invention is particularly suitable for use in OCT imaging.

OCT is an interferometric technique based on a broadband light source and coherent cross-correlation detection of light. The principles of OCT have been previously described (Huang et al., 1991). Although this invention provides many advantages over the prior art in performing OCT, the following U.S. patents are specifically incorporated herein by reference for the purposes of even further describing and enabling OCT instrumentation the use of OCT in scattering media: U.S. Pat. No. 5,991,697, No. 6,037,579, No. 6,252,666, No. 6,201,608 and No. 6,233,055; and for the purposes of even further describing and enabling OCT instrumentation and optical imaging techniques in general: U.S. Pat. No. 6,191,862, No. 6,160,826, No. 6,134,003, No. 6,111,645, No. 6,053,613, No. 6,004,314, No. 5,795,295, No. 5,501,226, No. 5,493,109, No. 5,465,147 and No. 5,549,114.

Exemplary applications besides imaging include, e.g., passing a guide wire through a coronary occlusion in interventional procedures, such as angioplasty. The invention also has applications in combination with photodynamic therapy and spectroscopic methods, such as Raman and reflectance spectroscopy, and in far red and near infrared laser ablation. Although the present invention provides numerous advantages, the use of near infrared (near-IR or NIR) in cardiovascular imaging is well established (Cassis and Lodder, 1993; Moreno et al., 2002).

Naturally, the present invention can also be used in connection with therapeutic or diagnostic imaging procedures in animals, particularly mammals. Other than humans, exemplary animals include valuable or valued animals, such as racehorses, domestic pets and endangered species. Further examples include animals used to directly produce (e.g., meat) or indirectly produce (e.g., milk) food for human consumption.

In addition to humans, another group of animals that the invention can be applied to is experimental animals, such as mice, rats, rabbits and such like, and also cats, dogs, sheep, pigs, etc. The use of the invention in such experimental animals is not limited to optimization in particular animal species before widespread application, but extends to testing in an experimental setting.

For example, the use of a genetically altered murine model for cardiovascular research has many advantages. First, murine heart function is similar to that in humans. Second, modest resource requirements make the model attractive for studies that require large sample sizes. Third, maturation is readily attained over a short period of time. Finally, because the murine genome is well characterized and can be easily modified, cardiovascular molecular mechanisms can be investigated through gene alterations.

A reliable imaging technique to determine regional wall thickening in intact beating mouse hearts had not been realized prior to the present invention. Conventional methods, such as ultrasound and MRI, are either too slow for murine heart rates, too expensive for everyday lab use, or do not provide sufficient spatial resolution for the small dimensions of the murine heart. The inventors reasoned that OCT, as a promising new technique, may be an appropriate imaging modality for murine cardiovascular studies. However, prior to the present invention, the application of OCT to imaging through blood-filled structures was severely limited. Through this invention, however, methods are now provided by which OCT can be applied to a dynamic, non-transparent biological structure, such as the murine cardiovascular system.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Low-Scattering, Oxygen-Carrying Blood Substitutes for Improved Imaging

The present example describes the criteria for designing or selecting low-scattering, oxygen-carrying blood substitutes for use in improved imaging and related light-based techniques, and the validation of the selection criteria in in vitro studies.

A. Methods

In vitro measurements were performed to determine the scattering and absorption properties of murine blood, blood substitute (Oxyglobin®), and dilutions of murine blood with Oxyglobin®. Oxyglobin® is isotonic to blood (prepared in a modified lactated Ringer's solution) and should not result in any hemolysis. An additional study was performed to specify the hematocrit reduction required for adequate visualization of the full RV thickness. For both studies, dilutions of fresh murine blood with Oxyglobin® (Biopure Corporation, Cambridge, Mass., www.biopure.com) were prepared to a hematocrit of 40, 30, 20, 10, 8, 5, and 3%. Pure blood (hematocrit>40%) and pure Oxyglobin® (hematocrit=0%) samples were also prepared.

A Cary 5E UV-Vis-NIR spectrophotometer (Varian, Australia, www.varianinc.com) with a single integrating sphere was used for scattering and absorption measurements. Cuvettes holding 0.4 ml with an average path length of 0.72 mm were constructed using two microscope slides and cover slips. Cuvettes containing the dilutions were placed in the spectrophotometer.

Spectral dependent transmittance and reflectance values were obtained from the spectrophotometer. An inverse adding-doubling program (Prahl et al., 1993; specifically incorporated herein by reference) was used to determine absorption ($\mu_a$) and reduced scattering ($\mu_s'$) coefficients. The total attenuation coefficient of blood can be represented as:

$$\mu_{total} = \mu_a + \mu_s \qquad [1]$$

While $\mu_s$ and $\mu_s'$ differ by a directional factor (Wilson, 1995), $\mu_s'$ is equivalent to the reciprocal distance between successive scattering events. Scattering is due to the presence of higher refractive index red blood cells in plasma while absorption is due to the presence of the chromophore hemoglobin (Twersky, 1970; Steinke and Sheppard, 1986). Blood from one or two (pooled) mice was used for each sample (n=4). Measurements were recorded at 20° C.

To determine the effect of OCT signal attenuation due to blood in the murine RV, dilutions were placed between two glass slides separated by a 0.15 mm air space. The 0.15 mm distance was selected as a compromise between obtaining sufficient signal amplitude from the lower surface at high hematocrit (e.g., 45%) and a measurable attenuation at low hematocrit (e.g., 5%). OCT images through the sample dilutions were recorded. Images were recorded for sample dilutions prepared at the same hematocrits as above, i.e., 40, 30, 20, 10, 8, 5, and 3%.

B. Results

The results of scattering and absorption measurements using whole murine blood and dilutions with Oxyglobin® are shown in FIG. 1A. Optical properties were determined at the OCT source wavelength $\lambda=1310$ nm. The scattering properties of whole murine blood decreased from $1.801\pm0.245$ to $0.253\pm0.176$ 1/mm (p<0.05) when the hematocrit was reduced from physiological levels to <5%. In contrast, the absorption properties of whole murine blood were similar over the same range, decreasing from $0.344\pm0.127$ to $0.129\pm0.118$ (p=NS). The results indicate that dilution of whole blood with Oxyglobin® reduces primarily scattering of light at 1310 nm.

The results of in vitro determination of the effect of OCT signal attenuation due to blood in the murine RV were determined using a slide assembly to record OCT images of blood dilutions. In the design of the study, two microscope slides separated by a 150 µm air gap were assembled and contained various blood/Oxyglobin® mixtures. The imaging beam was incident on the top microscope slide. Signal attenuation at the lower interface (relative to the upper surface) was calculated as a ratio and in decibels. The slides appear further apart when light propagates through Oxyglobin® compared to air. The greater apparent separation is due to the higher index of refraction of Oxyglobin®, necessitating a longer time to traverse the same physical distance.

The results from studies using the microscope slides are used to estimate the effect of OCT signal attenuation due to blood in the murine RV. Light attenuation in the intact murine RV with a fractional blood volume of 12.8% (Kahler et al., 1999) and a hematocrit of 45% is nearly equivalent to that in a 5% image (i.e., 0.12×0.45=5.4%) in the microscope slide study. From the 5% image, the inventors measured an attenuation of 0.214 (13.4 dB) over a 150 µm thickness. For a 450 µm thick RV murine myocardium (Scherrer-Crosbie et al., 1998), expected attenuation by blood is 40.2 dB ([13.4 dB×450 µm]/150 µm). The result indicates a substantial portion of the signal to noise ratio in the murine RV may be lost to scattering by blood.

Based on the foregoing calculations, the inventors reasoned that in vivo therapeutic and diagnostic imaging methods would be significantly improved by reducing the hematocrit to about 5% or less, whilst the oxygenation of the tissues should not be significantly reduced.

EXAMPLE 2

Improved OCT Myocardial Imaging with Low-Scattering Blood Substitutes

The present example in turns describes the successful in vivo imaging of cardiovascular tissues using low-scattering, oxygen-carrying blood substitutes prepared according to the selection criteria in Example 1.

A. Methods

1. OCT Instrumentation

The OCT system employed in the present example is based on a single-mode optical fiber Michelson interferometer and a semiconductor amplifier light source. The source has a center wavelength of 1310 nm and a spectral bandwidth of 60 nm. To visualize light incident on the murine myocardium with the unaided eye, a wavelength division multiplexer was used to combine 630 nm red light with 1310 nm source. A rapid scan optical delay line (Tearney et al., 1997) enables an image of a dynamic tissue, such as a beating murine heart, to be acquired at video rate. The axial and lateral resolutions were 16 µm and 12 µm, respectively. One A-scan (a depth scan) corresponded to 2 mm in air and comprised 5000 two-byte data samples, corresponding to a time of 2.5 ms at 2 MS/s sampling rate. Labview software (National Instruments, Austin, Tex.) was used to process acquired signals. A band-pass filter removed unwanted low and high frequency noise, and an incoherent demodulation method was used to compensate for non-linearities in the galvanometer scanning.

2. Animal Protocol

The protocol was approved by the Institutional Animal Care and Use Committee at The University of Texas at Austin and San Antonio, and conforms to "Guidelines for the Care and Use of Laboratory Animals" (NIH publication No. 86-23, revised in 1985) and "Principles of Laboratory Animal Care" (published by the National Society for Medical Research).

Female C57-B6 mice (n=6) weighing 19 to 22 g were anesthetized by administering urethane (1000 mg/kg, i.p.) and etomidate (25 mg/kg, i.p.). Respiration was controlled through a tracheotomy cannula and the animals were mechanically ventilated with 100% $O_2$ at 95 breaths per min using a rodent ventilator (Harvard Apparatus Model 683, South Natck, Mass.). Needle electrodes were applied subcutaneously and connected to a Microelectrode AC amplifier (Model 1800, A-M Systems, Carlsborg, Wash.) for ECG recording. The chest was entered by an anterior thoracotomy. An apical stab was made in the left ventricle with a 27-G needle, through which Oxyglobin® was introduced into the bloodstream. A right neck cutdown was performed and the right jugular vein exposed. The right jugular vein was nicked for blood removal, or compressed for hemostasis. Separate sites to infuse Oxyglobin® and bleed the mouse were chosen so the intravascular exchange could be performed simultaneously. In this fashion, any potential hemodynamic instability was minimized.

The OCT light source was aimed at the right ventricular mid-free wall with the red aiming beam. Baseline images were recorded at the native hematocrit. Hematocrit was determined by centrifugation followed by comparison to a calibration chart. Oxyglobin® was used to replace whole blood in a 1:1 fashion, in amounts of approximately 300 µl at a time. This process was continued until a hematocrit of less than 5% was obtained, as indicated in the design studies of Example 1. Images were recorded as described above and processed offline.

3. Image Processing

To determine the epicardial and endocardial boundaries, gray-scaled images were converted to binary images. Application of two-dimensional median, closed and open filters was necessary to avoid speckling effects present in the binary image. Subtracting depth positions of the two boundaries yielded an instantaneous thickening fraction that was then low-pass filtered to derive a thickening vs. time curve.

As OCT measures optical path length, thickness was scaled according to a weighted average of the indices of refraction for myocardium and Oxyglobin®. An average index of refraction of 1.343 for Oxyglobin® was measured by comparing measured OCT thickness to the actual thickness (Tearney et al., 1995; Wang et al., 1996). A published refractive index value of human LV myocardium (1.382 at 1300 nm) was used for murine myocardium (Tearney et al., 1995). End diastolic thickness (EDT) was determined by noting the time of the R-wave peak on the surface ECG. End systolic thickness (EST) was determined at the point of maximal thickness. Both EST and EDT values were averaged over 4-6 beats.

4. Statistics

A two-tailed, Student's paired t-test was used to compare the EDT and EST, baseline and Oxyglobin® hematocrit, and baseline and Oxyglobin® heart rates. Level of significance was taken as p<0.05. Data are presented as mean±SD.

B. Results and Discussion

After reduction of hematocrit to below 5%, thickness measurements of the right ventricles in the intact beating murine heart became possible using OCT imaging. The resultant thickness measurements from OCT imaging at less than 5% hematocrit are shown in Table 1. The HR in the presence of whole blood was 288±40 bpm at baseline and 312±42 bpm (p=NS) after Oxyglobin® reduced the hematocrit to less than 5%. At the reduced hematocrit, the preparation was viable for several hours. The whole blood hematocrit was 52.4±3.8% at baseline and was reduced to 3.7±1.2% after replacement with Oxyglobin®. The end-diastolic thickness of the RV free wall was 0.352±0.047 μm and the end-systolic thickness was 0.458±0.051 μm (p<0.01). These values were determined after reduction of the hematocrit, since the RV endocardial boundary could not be identified in the presence of whole blood.

TABLE 1

|  | HR | EDT (mm) | EST (mm) | % TF | Hct |
|---|---|---|---|---|---|
| Baseline Whole blood | 288 ± 40 | NA | NA | NA | 52.4 ± 3.8% |
| Hemoglobin Solution | 312 ± 42 | ‡0.352 ± 0.047 | 0.458 ± 0.051 | 30.8 ± 7.5 | 3.7 ± 1.2% |

‡–p < 0.001; EDT vs. EST
RV end-systolic and end-diastolic thicknesses (EST and EDT) and thickening fraction (% TF) after isovolumic blood replacement with hemoglobin solution blood substitute in mice (n = 6). Measurements were not possible before replacement. Values are presented as mean ± SD.

OCT images of the RV wall were determined at baseline in the presence of whole blood and after reduction of the hematocrit to less than 5% with Oxyglobin®. In these studies, the epicardial boundary was easily delineated in both baseline and low hematocrit images. However, the endocardial boundary is only visible in the low hematocrit images. Epicardial motion was observed to increase at low hematocrit in several of the images.

A comparison of thickening versus time was determined in these studies. Wall thickness measurements and surface ECGs were determined from all six mice. Thickness measurements were only available after hematocrit reduction with Oxyglobin®. Each measurement was recorded over one second. Instantaneous right ventricular wall thickening and surface ECG were possible after reducing the hematocrit to less than 5% with Oxyglobin®. The peak of the R-wave of the ECG occurs at the thinnest portion of the thickening curve in every image, as expected. The percent thickening for the group was 30.8±7.5% (Table 1).

The data in the present example demonstrates for the first time that OCT can be used in conjunction with a blood substitute to measure instantaneous murine RV myocardial thickening. Two distinct approaches to reduce scattering by blood have been tested earlier. However, prior to the present invention, the problem of light scattering due to blood was not overcome.

One previous study attempted to increase the refractive index of plasma to approach that of red blood cells (Brezinski et al., 2001). However, even using a simple in vitro system in which blood is pumped through transparent tubing, neither of the compounds tested were able to reduce scattering sufficiently such that they could be used in vivo or at practical volumes (Brezinski et al., 2001). The other earlier approach was to attempt to reduce attenuation due to scattering in the optical path using a saline bolus injection (Fujimoto et al., 1999). Since a saline bolus reduces oxygenation and only allows imaging for a short time duration, the present inventors realized that a different approach was needed to prevent ischemia.

The inventors decided to replace red blood cells with a low- or non-scattering, oxygen-carrying blood substitute, thereby removing the scattering objects (red blood cells), yet maintaining oxygenation. The modified hemoglobin-based blood substitutes used in the present example were chosen because they are already approved for veterinary use and are expected to soon be approved for clinical use by the FDA (Lok, 2001). Therefore, regular use of such substances for many surgical and diagnostic procedures is feasible. Though total volume replacement was not expected during the development of blood substitutes (Spahn and Pasch, 2001), the physiological impact of such an exchange transfusion (down to ~2% Hct) has been determined in sheep (Vlahakes et al., 1990). Post-replacement hemodynamics were stable and animals survived with eventual regeneration of erythrocytes.

In OCT imaging, light must penetrate the structure being studied. Light attenuation derives from both scattering and absorption. Results presented in FIG. 1A indicate that red blood cells are a significant source of scattering, and a marked reduction in hematocrit is required for light to penetrate the distance needed to image the intact murine RV. The data confirmed the inventors' hypothesis, showing that reduced light attenuation due to scattering could be accomplished by Oxyglobin® blood substitution. The use of such artificial hemoglobins therefore allows the maintenance of physiological properties of the heart and other tissues during OCT imaging.

Although an understanding is not necessary to the practice of the invention, the inventors choose to comment on the slight but non-significant decrease observed in absorption as a function of hematocrit. The inventors' working hypothesis is that the effect is due to a decrease in hemoglobin concentration. Typical physiological values for hemoglobin concentration are from 134-173 g/L (Roggan et al., 1999). According to manufacturer specifications, Oxyglobin® has a hemoglobin concentration of 130 g/L, indicating a concentration decrease in the replacement process. Clearly, however, decreased absorption was a much smaller factor in signal improvement than was scattering over the range of hematocrit examined.

Table 1 presents RV thickening measurements after the incorporation of the blood substitute. Previously published results (Scherrer-Crosbie et al., 1998) of mean RV thickness measured with transesophageal echocardiography and MRI (0.41±0.11 mm and 0.46±0.10 mm, respectively) agree closely with the values in the present example. Attempts to quantify RV thickening fraction (% TF) in other mammals yielded 25% in humans (Bolli et al., 1990) and 14.1% in the canine RV (Meier et al., 1980). These results are also similar to those found for the murine RV in the current study.

Possible sources of error in thickness measurements include an imprecise geometry between the beam and myocardium. During a heartbeat, some solid body rotation occurs so the instantaneous measured thickness will be different from the true thickness by the cosine of the angle between the normal of the heart surface and the beam (e.g., 0.4% for a 5° deviation). In addition, the thickness value depends on the average index of refraction used to convert measured optical path length to physical thickness. The inventors used a weighted average of refractive index between myocardium and the blood substitute (Duck, 1990). In addition to the aforementioned errors, RV thickness varies along the axis of the chamber. Measurements made at the canine conus and apex differ significantly from those made at the mid-ventricular free wall (Meier et al., 1980). The inventors attempted to visibly align the beam at the mid-ventricular level, but the exact position may have deviated.

Imaging depths for OCT have been demonstrated at 1-2 mm in highly scattering tissues such as skin (Schmitt et al., 1995). Consequently, one might expect a penetration depth greater than the thickness of the RV, which is near 0.45 mm (Scherrer-Crosbie et al., 1998). Because the computed signal attenuation by blood in the murine RV is substantial (40.2 dB), expected signal attenuation (double pass) from the endocardium is severe and identification of the boundary difficult. This was demonstrated experimentally.

In the OCT images of the RV wall determined at baseline, a clear epicardial boundary was observed in whole blood images. Since the change in the refractive index of air (n=1) to myocardium (n≈1.38) is large, the inventors expected and observed a well-delineated epicardial boundary. OCT measures the intensity of back-scattered light that occurs at such a change in index of refraction. The contrast at the endocardial boundary, however, is substantially reduced. First, as the inventors' calculation indicates severe light attenuation (40.2 dB) occurs with a double pass through the myocardium, so the back-reflected signal amplitude is substantially reduced. Second, the index of refraction change at the endocardium/blood boundary is small compared to the air/epicardium boundary. The refractive index of myocardium is much closer to blood than air. Only after hemodilution with Oxyglobin to 5% hematocrit was light attenuation reduced sufficiently so that the full thickness of the RV could be imaged.

Since blood does not account for the majority of myocardial volume (12.8%, Kahler et al., 1999), it is a further surprising aspect of the invention that diminishing only the scattering coefficient of the blood would result in such a dramatic improvement in RV imaging depth. However, the inventors estimated an expected attenuation due to scattering of OCT light by blood from the results obtained in the microscope slide studies. As described above, the expected attenuation from blood alone in a 450 μm thick murine RV (Scherrer-Crosbie et al., 1998) is approximately 100 times (40.2 dB). Because the reflection amplitude from the inner myocardial wall of the right ventricle will be less than that from the glass-liquid boundary in the microscope slide studies, the inventors expect the signal amplitude (from the endocardium) will be reduced more than 100 times relative to the air-myocardial interface. Taken together, these results indicate that substantial attenuation due to scattering by blood may be neutralized by reducing the hematocrit. With this technique, one can increase signal amplitude sufficiently to reveal the full thickness of the murine RV myocardium in OCT images.

Many investigators have recognized the potential advantages of applying optical techniques to diagnose and treat cardiovascular diseases. For example, optical techniques have been applied to assist in passing a guide wire through total coronary occlusions in interventional procedures (Neet et al., 2000). Photodynamic therapy is being investigated as a potential approach to effect a cytotoxic response in atherosclerotic plaque (Rockson et al., 2000). Inasmuch as spectroscopic methods are capable of providing biochemical specific information on tissue composition, reflectance and Raman techniques have been applied to cardiovascular diagnostics with various degrees of success (Naghavi et al., 2000; Romer et al., 1998; Brennan et al., 1997). More recently, OCT has been used in attempts to record depth-resolved images of fibrous lesions on the surface of coronary arteries (Brezinksi et al., 1996; Patwari et al., 2000).

A limitation of such optical techniques is the strong attenuation due to scattering by blood that is frequently positioned between the probe and targeted tissue structure. Based on the results of the present invention, the application of these techniques can now be better facilitated by the use of a blood-substitute with a scattering attenuation coefficient less than that of blood. An alternative class of agents, perfluorocarbon emulsions, has been proposed as a blood substitute (Spahn and Pasch, 2001). Because the emulsions contain particles, however, light attenuation due to Rayleigh scattering will reduce the back-reflected signal amplitude, making perfluorocarbon emulsions in their current form unsuitable for such uses.

In conclusion, low-scattering, oxygen-carrying blood substitutes, as exemplified by hemoglobin solutions, can now be used to substantially improve optical imaging conditions in blood-filled tissues. Improved imaging is possible because the light attenuation due to blood scattering is significantly diminished. The use of such blood substitutes provides a solution to the light scattering problems due to blood in light-based in vivo therapeutic and imaging methods, including OCT imaging, and further solves the problem of reduced oxygenation, such that such techniques can be applied to the cardiovascular system, brain and other blood-rich tissues.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bolli, Hartley, Chelly, et al., "An accurate, nontraumatic ultrasonic method to monitor myocardial wall thickening in patients undergoing cardiac surgery," *J. Am. Coll. Cardiol.*, 15:1055-65, 1990.

Boppart, Tearney, Bouma, et al., "Noninvasive assessment of the developing *Xenopus* cardiovascular system using optical coherence tomography," *Proc. Natl. Acad. Sci. USA*, 94:4256-4261, 1997.

Brennan, Romer, Lees, et al., "Determination of human coronary artery composition by Raman spectroscopy," *Circulation*, 96:99-105, 1997.

Brezinksi, Tearney, Bouma, et al., "Imaging of coronary artery microstructure (in vitro) with optical coherence tomography," *Am. J. Cardiol.*, 77:92-93, 1996.

Brezinski, Saunders, Jesser, et al., "Index matching to improve optical coherence tomography imaging through blood," *Circulation*, 103:1999-2003, 2001.

Cassis and Lodder, "Near-IR imaging of atheromas in living arterial tissue", *Anal. Chem.*, 65:1247-1256, 1993.

Chen, Milner, Srinivas, et al., "Noninvasive imaging of in vivo blood flow velocity using optical Doppler tomography," *Optics Letters*, 22(14):1119-21, 1997.

Duck, "In: Physical properties of tissue: a comprehensive reference book," Academic Press, Inc., San Diego, 43-139, 1990.

Fishman et al., *Investigative Radiology*, 24:65-71, 1999.

Fujimoto, Boppart, Tearney, et al., "High resolution in vivo intra-arterial imaging with optical coherence tomography," *Heart*, 82:128-133, 1999.

Hee, Izatt, Swanson, et al., "Optical coherence tomography of the human retina," *Acrh. Ophthalmol.*, 113:326-332, 1995.

Huang, Swanson, Lin, et al., "Optical coherence tomography," *Science*, 254: 1178-1181, 1991.

Joseph et al., *Investigative Radiology*, 20:504-509, 1995.

Kahler, Waller, Rommel, et al. "Perfusion-corrected mapping of cardiac regional blood volume in rats in vivo," *Magnetic Resonance in Medicine*, 42:500-506, 1999.

Kramer, Elam, Saxton, et al., "Influence of oxygen saturation, erythrocyte concentration and optical depth upon the red and near-infrared light transmittance of whole blood," *Am. J. Physiol.*, 165:229-246, 1951.

Lok, "Blood product from cattle wins approval for use in humans," *Nature*, 410(6831):855, 2001.

Meier, Bove, Santamore, et al., "Contractile function in canine right ventricle," *Am. J. Physiol.*, 239(8):H794-H804, 1980.

Moreno, Lodder, Purushothaman, et al., "Detection of lipid pool, thin fibrous cap, and inflammatory cells in human aortic atherosclerotic plaques by near infrared spectroscopy", *Circulation*, 105:923-927, 2002.

Naghavi, Khan, Gu, et al., "On application of IR and NIR fiber optic imaging in thermographic and spectroscopic diagnosis of atherosclerotic vulnerable plaques: preliminary experience," *Proceedings of SPIE*, 4130; 659-672, 2000.

Neet, Winston, Hedrick, et al., "Navigating a guide wire through total occlusions: clinical experience," *Proceedings of the SPIE*, 3907:536-543, 2000.

Patwari, Weissman, Boppart, et al., "Assessment of coronary plaque with optical coherence tomography and high-frequency ultrasound," *Am. J. Cardiol.*, 85:641-644, 2000.

Prahl, van Gemert, Welch, "Determining the optical properties of turbid media by using the adding-doubling method," *Appl. Opt.*, 32(4):559-568, 1993.

Rockson, Lorenz, Cheong, et al., "Photoangioplasty: an emerging clinical cardiovascular role for photodynamic therapy," *Circulation*, 102:591-596, 2000.

Roggan, Friebel, Dörschel, "Optical properties of circulating human blood in the wavelength range 400-2500 nm," *J. Biomed. Optics*, 4(1):36-46, 1999.

Rollins, Kulkarni, Yazdanfar, et al., "In vivo video rate optical coherence tomography," *Optics Express*, 3(6):219-229, 1998.

Romer, Brennan, Fitzmaurice, et al., "Histopathology of human coronary atherosclerosis by quantifying its chemical composition with Raman spectroscopy," *Circulation*, 97:878-885, 1998.

Saito et al., *J. Cardiography*, 14:677-688, 1984.

Scherrer-Crosbie, Steudel, Hunziker, et al. "Determination of right ventricular structure and function in normoxic and hypoxic mice," *Circulation*, 98:1015-1021, 1998.

Schmitt, Yadlowsky, Bonner, "Subsurface imaging in living skin with optical coherence tomography," *Dermatol.*, 191: 93-98, 1995.

Spahn and Pasch, "Physiological properties of blood substitutes," *News Physiol. Sci.*, 16:38-41, 2001.

Steinke and Sheppard, "Role of light scattering in whole blood oximetry," *IEEE Trans. Biomed. Eng.*, 33:294-301, 1986.

Stowell, Levin, Spiess and Winslow, "Progress in the development of RBC substitutes," *Transfusion*, 41:287-299, 2001

Tearney, Brezinski, Southern, et al., "Determination of the refractive index of highly scattering human tissue by optical coherence tomography," *Optics Letters*, 20(21):2258-2260, 1995.

Tearney, Bouma, Fujimoto, "High-speed phase- and group-delay scanning with a grating-based phase control delay line," *Optics Letters*, 22(23):1811-1813, 1997.

Twersky, "Absorption and multiple scattering by biological suspensions," *J. Opt. Soc. Amer.*, 60:1084-1093, 1970.

Vlahakes, Lee, Jacobs Jr., et al., "Hemodynamic effects and oxygen transport properties of a new blood substitute in a model of massive blood replacement," *J. Thor. Cardio. Surg.*, 100(3):379-88, 1990.

Wang, Milner, Change, et al., "Group refractive index measurement of dry and hydrated type I collagen films using optical low coherence reflectometry," *J. Biomed. Optics*, 1(2); 212-216, 1996.

Wilson, "Chapter 8: Measurements of Optical Properties. In: Optical-thermal response of laser-irradiated tissue," Welch and van Gemert, eds., Plenum Press, New York and London. p 233, 1995.

What is claimed is:

1. A method for performing optical imaging or light-based treatment of at least a first tissue in an animal, comprising providing into the blood associated with said at least a first tissue a biologically effective amount of a low-scattering, oxygen-carrying blood substitute, wherein the low-scattering, oxygen-carrying blood substitute substantially reduces optical scattering from the blood fraction whilst substantially maintaining tissue oxygenation, and applying an optical imaging or light-based treatment step to said at least a first tissue.

2. The method of claim 1, wherein said low-scattering, oxygen-carrying blood substitute is a substantially non-particulate hemoglobin solution.

3. The method of claim 2, wherein said hemoglobin solution is a substantially non-particulate, homogeneous, acellular hemoglobin solution.

4. The method of claim 2, wherein said hemoglobin solution comprises bovine, porcine, ovine or primate hemoglobin.

5. The method of claim 2, wherein said hemoglobin solution comprises human hemoglobin.

6. The method of claim 2, wherein said hemoglobin solution comprises recombinantly produced hemoglobin.

7. The method of claim 2, wherein said hemoglobin solution comprises crosslinked hemoglobin.

8. The method of claim 2, wherein said hemoglobin solution comprises polymerized hemoglobin.

9. The method of claim 2, wherein said hemoglobin solution comprises glutaraldehyde crosslinked, polymerized hemoglobin.

10. The method of claim 2, wherein said hemoglobin solution comprises surface modified hemoglobin.

11. The method of claim 2, wherein said hemoglobin solution has a hemoglobin concentration of at least about 70% of the hemoglobin concentration of whole blood.

12. The method of claim 1, wherein provision of said low-scattering, oxygen-carrying blood substitute reduces the hematocrit of the blood associated with said at least a first tissue at least to about 10%.

13. The method of claim 12, wherein provision of said low-scattering, oxygen-carrying blood substitute reduces the hematocrit of the blood associated with said at least a first tissue at least to about 5%.

14. The method of claim 13, wherein provision of said low-scattering, oxygen-carrying blood substitute reduces the hematocrit of the blood associated with said at least a first tissue at least to about 4%.

15. The method of claim 14, wherein provision of said low-scattering, oxygen-carrying blood substitute reduces the hematocrit of the blood associated with said at least a first tissue at least to about 3%.

16. The method of claim 15, wherein provision of said low-scattering, oxygen-carrying blood substitute reduces the hematocrit of the blood associated with said at least a first tissue at least to about 2%.

17. The method of claim 16, wherein provision of said low-scattering, oxygen-carrying blood substitute reduces the hematocrit of the blood associated with said at least a first tissue at least to about 1%.

18. The method of claim 1, wherein provision of said low-scattering, oxygen-carrying blood substitute reduces the hematocrit of the blood associated with said at least a first tissue to between 0 and about 10%.

19. The method of claim 18, wherein provision of said low-scattering, oxygen-carrying blood substitute reduces the hematocrit of the blood associated with said at least a first tissue to between 1 and about 5%.

20. The method of claim 1, wherein provision of said low-scattering, oxygen-carrying blood substitute reduces the hematocrit of the blood associated with said at least a first tissue to an amount effective to result in a half maximal or lower scattering coefficient $\mu_s'$ according to the equation $\mu_{tot}' = \mu_a + \mu_s'$, where $\mu_a$ is the absorption coefficient and $\mu_{tot}'$ is the total attenuation coefficient.

21. The method of claim 1, wherein provision of said low-scattering, oxygen-carrying blood substitute reduces the hematocrit of the blood associated with said at least a first tissue to an amount effective to result in a scattering coefficient of about half the scattering coefficient for whole blood or less.

22. The method of claim 1, wherein said low-scattering, oxygen-carrying blood substitute is a solution comprising at least a first oxygen carrier, and wherein the largest species in said solution has a size of about 6 nanometers.

23. The method of claim 1, wherein provision of said low-scattering, oxygen-carrying blood substitute reduces the scattering coefficient of the blood associated with said at least a first tissue to about one half of the scattering coefficient of whole blood or less at a sample wavelength of between about 600 nm and about 1500 nm.

24. The method of claim 23, wherein provision of said low-scattering, oxygen-carrying blood substitute reduces the scattering coefficient of the blood associated with said at least a first tissue to about one tenth of the scattering coefficient of whole blood or less at a sample wavelength of between about 600 nm and about 1500 nm.

25. The method of claim 23, wherein provision of said low-scattering, oxygen-carrying blood substitute reduces the scattering coefficient of the blood associated with said at least a first tissue to about one half of the scattering coefficient of whole blood or less at a sample wavelength of about 600 nm.

26. The method of claim 25, wherein provision of said low-scattering, oxygen-carrying blood substitute reduces the scattering coefficient of the blood associated with said at least a first tissue to about one tenth of the scattering coefficient of whole blood or less at a sample wavelength of about 600 nm.

27. The method of claim 23, wherein provision of said low-scattering, oxygen-carrying blood substitute decreases the scattering coefficient of the blood associated with said at least a first tissue to a scattering coefficient of about 0.4 mm$^{-1}$ or less at about 1310 nm.

28. The method of claim 27, wherein provision of said low-scattering, oxygen-carrying blood substitute decreases the scattering coefficient of the blood associated with said at least a first tissue to a scattering coefficient of about 0.3 mm$^{-1}$ or less at about 1310 nm.

29. The method of claim 28, wherein provision of said low-scattering, oxygen-carrying blood substitute decreases the scattering coefficient of the blood associated with said at least a first tissue to a scattering coefficient of about 0.2 mm$^{-1}$ at about 1310 nm.

30. The method of claim 1, wherein said low-scattering, oxygen-carrying blood substitute is a solution comprising at least a first oxygen carrier, and wherein the refractive index of said oxygen carrier is substantially equal to other molecular species in solution.

31. The method of claim 1, wherein said low-scattering, oxygen-carrying blood substitute has at least about 70% of the oxygen carrying capacity of whole blood.

32. The method of claim 1, wherein said at least a first tissue is neural tissue.

33. The method of claim 1, wherein said at least a first tissue is brain tissue.

34. The method of claim 1, wherein said at least a first tissue is located within a highly perfused organ.

35. The method of claim 34, wherein said at least a first tissue is located within the kidney, lung, liver, spleen, brain, heart or one of the great vessels.

36. The method of claim 1, wherein said at least a first tissue is cardiovascular tissue.

37. The method of claim 1, wherein said at least a first tissue is cardiac tissue.

38. The method of claim 1, wherein said at least a first tissue is a blood vessel.

39. The method of claim 38, wherein said optical imaging or treatment step is applied from the lumen of said blood vessel.

40. The method of claim 38, wherein said blood vessel has or is suspected to have an atherosclerotic plaque or lesion.

41. The method of claim 1, wherein said at least a first tissue comprises at least two tissue layers, and wherein at least a first of said tissue layers is associated with a substantial blood fraction.

42. The method of claim 41, wherein said at least a first tissue comprises a plurality of tissue layers, and wherein at least a first of said tissue layers is associated with a substantial blood fraction.

43. The method of claim 1, wherein said animal has, or is at risk for developing, a cardiac tissue or cardiac valve defect.

44. The method of claim 1, wherein said animal has suffered, or is at risk for developing, a heart attack.

45. The method of claim 1, wherein said animal has, or is at risk for developing, an ischemic tissue.

46. The method of claim 1, wherein said animal has suffered, or is at risk for developing, a stroke.

47. The method of claim 1, wherein said animal has, or is at risk for developing, a vascularized tumor.

48. The method of claim 1, wherein said animal is a mouse.

49. The method of claim 1, wherein said animal is a human subject.

50. A method for optical coherence tomography imaging of a tissue in an animal, which tissue comprises a substantial blood fraction, comprising: (a) introducing into said blood fraction of said tissue an amount of an essentially non-particulate hemoglobin solution effective to substantially reduce optical scattering from said blood fraction whilst substantially maintaining oxygenation in said tissue; and (b) performing optical coherence tomography imaging of said tissue.

51. A method for performing optical imaging or treatment of a tissue in an animal, which tissue comprises a substantial blood fraction, comprising: (a) introducing into said blood fraction of said tissue an amount of a low-scattering, oxygen-carrying blood substitute effective to substantially reduce optical scattering from said blood fraction whilst substantially maintaining oxygenation in said tissue, wherein the low-scattering, oxygen-carrying blood substitute reduces the scattering coefficient of the blood associated with said at least a first tissue to about one half of the scattering coefficient of whole blood or less at a sample wavelength of between about 600 nm and about 1500 nm; and (b) applying an optical imaging or treatment step to said tissue.

52. A method for performing optical imaging of at least a first tissue in an animal, comprising providing into the blood associated with said at least a first tissue a biologically effective amount of a low-scattering, oxygen-carrying blood substitute, wherein the low scattering, oxygen carrying blood substitute includes a size less than about 80 nm to substantially reduce optical scattering, and applying an optical imaging step to said at least a first tissue.

53. A method of generating an image of at least a first vascularized tissue by in vivo diagnostic light imaging, comprising providing into the blood perfusing said vascularized tissue a biologically effective amount of a low-scattering, oxygen-carrying blood substitute, wherein the biologically effective amount results in a reduced scattering coefficient of whole blood to about 66% to 5%, and executing a diagnostic light imaging technique to generate an image of said vascularized tissue.

54. A method for optical coherence tomography imaging of at least a first tissue in an animal, comprising providing into the blood associated with said at least a first tissue a biologically effective amount of a substantially low-scattering between non-particulate hemoglobin solution, and performing optical coherence tomography imaging of said at least a first tissue.

* * * * *